US011344617B2

(12) United States Patent
Vermeij et al.

(10) Patent No.: US 11,344,617 B2
(45) Date of Patent: May 31, 2022

(54) LIQUID VACCINES OF LIVE ENVELOPED VIRUSES

(71) Applicant: Intervet Inc., Madison, NJ (US)

(72) Inventors: Paul Vermeij, St. Anthonis (NL); Edwin Kets, Heilig Landstichting (NL); Chris Dirks, Gemert (NL); Martin Piest, Afferden (NL)

(73) Assignee: Intervet Inc., Madison, NJ (US)

( * ) Notice: Subject to any disclaimer, the term of this patent is extended or adjusted under 35 U.S.C. 154(b) by 0 days.

(21) Appl. No.: 16/769,820

(22) PCT Filed: Dec. 21, 2018

(86) PCT No.: PCT/EP2018/086582
§ 371 (c)(1),
(2) Date: Jun. 4, 2020

(87) PCT Pub. No.: WO2019/122329
PCT Pub. Date: Jun. 27, 2019

(65) Prior Publication Data

US 2020/0368346 A1 Nov. 26, 2020

(30) Foreign Application Priority Data

Dec. 22, 2017 (EP) .................................... 17210395

(51) Int. Cl.

| | |
|---|---|
| ***A61K 39/155*** | (2006.01) |
| ***C12N 7/00*** | (2006.01) |
| ***A61K 39/12*** | (2006.01) |
| ***A61K 9/08*** | (2006.01) |
| ***A61K 47/18*** | (2017.01) |
| ***A61K 47/26*** | (2006.01) |
| ***A61K 47/10*** | (2017.01) |
| ***A61K 39/175*** | (2006.01) |
| ***A61K 39/215*** | (2006.01) |
| ***A61K 39/245*** | (2006.01) |
| ***A61K 47/22*** | (2006.01) |
| *A61K 39/00* | (2006.01) |

(52) U.S. Cl.

CPC .............. *A61K 39/155* (2013.01); *A61K 9/08* (2013.01); *A61K 39/12* (2013.01); *A61K 39/175* (2013.01); *A61K 39/215* (2013.01); *A61K 39/245* (2013.01); *A61K 47/10* (2013.01); *A61K 47/186* (2013.01); *A61K 47/22* (2013.01); *A61K 47/26* (2013.01); *C12N 7/00* (2013.01); *A61K 2039/525* (2013.01); *A61K 2039/54* (2013.01); *A61K 2039/543* (2013.01); *C12N 2710/16034* (2013.01); *C12N 2760/00034* (2013.01); *C12N 2760/18034* (2013.01); *C12N 2760/18434* (2013.01); *C12N 2760/18634* (2013.01); *C12N 2770/20034* (2013.01)

(58) Field of Classification Search
None
See application file for complete search history.

(56) References Cited

U.S. PATENT DOCUMENTS

| | | | | |
|---|---|---|---|---|
| 8,247,198 | B2 | 8/2012 | Gorke et al. | |
| 2013/0129685 | A1* | 5/2013 | Drew .................. | A61K 47/183 424/93.6 |
| 2015/0246114 | A1 | 9/2015 | Qiao et al. | |
| 2020/0368346 | A1* | 11/2020 | Vermeij ................ | A61K 47/10 |

FOREIGN PATENT DOCUMENTS

| | | | |
|---|---|---|---|
| EP | 2552478 | B1 | 12/2016 |
| JP | 2013524782 | A | 6/2013 |
| JP | 2015526450 | A | 9/2015 |
| WO | 2009120839 | A2 | 10/2009 |
| WO | 2011155829 | A1 | 12/2011 |
| WO | 2014029702 | A1 | 2/2014 |
| WO | 2014131906 | A1 | 9/2014 |
| WO | 2014140239 | A1 | 9/2014 |
| WO | 2015121463 | A2 | 8/2015 |

OTHER PUBLICATIONS

Correia, Ricardo, et al. "Improved storage of influenza HA-VLPs using a trehalose-glycerol natural deep eutectic solvent system." Vaccine (2021).*
Marchel et al. "Purification of virus-like particles using aqueous biphasic systems composed of natural deep eutectic solvents." Separation and Purification Technology 252 (2020): 117480.*
Ausar, SF et al., High-throughput screening of stabilizers for respiratory syncytial virus: identification of stabilizers and their effects on the conformational thermostability of viral particles., Human Vaccines, 2007, pp. 94-103, 3(3).
Burke, Carl J., Formulation, Stability, and Delivery of Live Attenuated Vaccines for Human Use, Critical Reviews in Therapeutic Drug Carrier Systems, 1999, 1-83, 16(1).
Abbott, Andrew P. et al., Novel solvent properties of choline chloride/urea mixtures, Chem. Commun., 2003, 70-71, 1.
Byrne, N.. et al., Enhanced stabilization of the Tobacco mosaic virus using protic ionic liquids, Phys. Chem. Chem. Phys., 2012, pp. 10119-10121, 14.
Choi, Young Hae et al., Are Natural Deep Eutectic Solvents the Missing Link in Understanding Cellular Metabolism and Physiology?, Plant Physiology, 2011, 1701-1705, 156.

(Continued)

*Primary Examiner* — Shanon A. Foley
(74) *Attorney, Agent, or Firm* — Michael D. Davis

(57) ABSTRACT

The present invention describes a liquid vaccine composition of a live enveloped virus and a pharmaceutically acceptable carrier, whereby the carrier is a natural deep-eutectic solvent (NADES), and the vaccine has a water activity of less than about 0.8. The NADES provides a stabilisation of the sensitive virus for prolonged time and at ambient temperature. In general, the liquid vaccine compositions according to the invention, in different compositions for the various enveloped viruses, show remarkable capabilities of stabilisation. This overcomes the need for lyophilisation, a great economic benefit. Also the liquid nature of the vaccines facilitates administration to human or animal targets.

11 Claims, 8 Drawing Sheets

(56) References Cited

OTHER PUBLICATIONS

Figure 1:
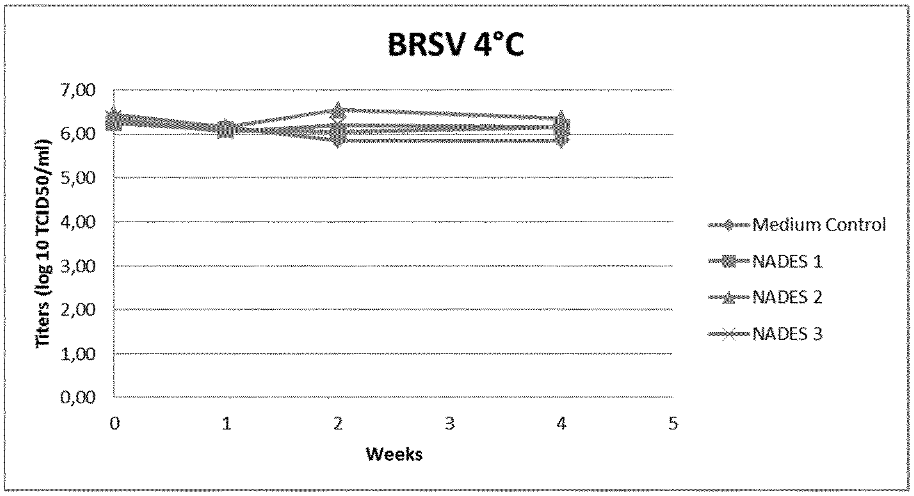
Figure 1:
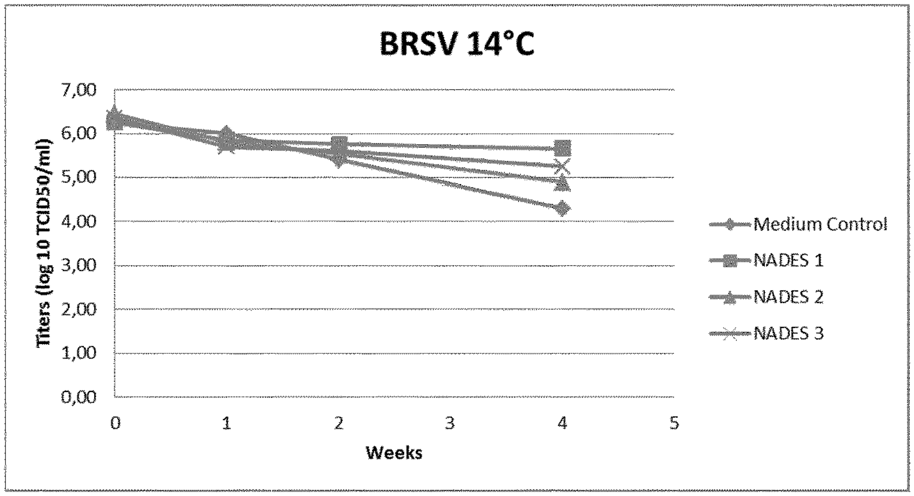
Figure 1:
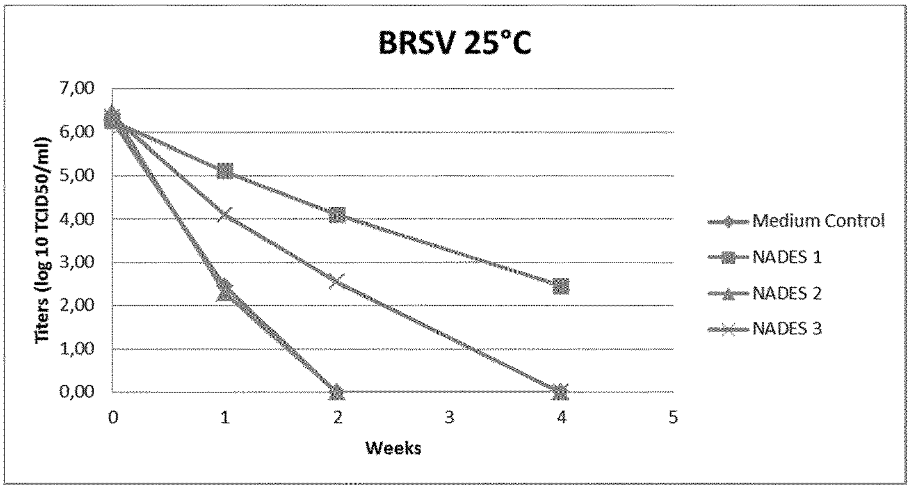

Dai, Y. et al., Natural deep eutectic solvents as new potential media for green technology, Analytica Chimica Acta, 2013, pp. 61-68, 766.
Dai, Y., et al., Ionic Liquids and Deep Eutectic Solvents in Natural Products Research: Mixtures of Solids as Extraction Solvents, Journal of Natural Products, 2013, pp. 2162-2173, 76.
Dai, Y., et al., Natural Deep Eutectic Solvents as a New Extraction Media for Phenolic Metabolites in *Carthamus tinctorius* L., Analytical Chemistry, 2013, pp. 6272-6278, 85.
Dai, Y., et al., Tailoring properties of natural deep eutectic solvents with water to facilitate their applications, Food Chemistry, 2015, pp. 14-19, 187.
Extended European Search Report for 17210395.4 dated Mar. 19, 2018.
FAO Agricultural Services Bulletin 149, Technical manual, "Handling and preservation of fruits and vegetables by combined methods for rural areas", Chapter 3, 18 pages.
International Search report for PCT/EP2018/086582 received on Mar. 25, 2019, 13 pages.
Obluchinskaya, E.D. et al., Natural Deep Eutectic Solvents as Alternatives for Extracting Phlorotannins from Brown Algae, Pharmaceutical Chemistry Journal, 2019, 243-247 (Russian Original vol. 53, No. 3, pp. 45-49, Mar. 2019—translated from Khimiko-Farmatseviticheskii Zhurnal, vol. 53, No. 3, pp. 45-49, Mar. 2019), 53(3).
Zakrewsky, M. et al., Choline and geranate deep eutectic solvent as a broad-spectrum antiseptic agent for preventive and therapeutic applications, Advanced Healthcare Materials, 2016, 1282-1289, 5(11).

* cited by examiner

A

B

C

A

B

C

A

B

C

A

BRSV 4°C

- Medium control
- Bet:Suc:WFI 2:1:6.4
- Pro:Sor:WFI 2:1:4
- Cho:Xyl:WFI 2:1:3

B

BRSV 14°C

- Medium control
- Bet:Suc:WFI 2:1:6.4
- Pro:Sor:WFI 2:1:4
- Cho:Xyl:WFI 2:1:3

C

BRSV 25°C

- Medium control
- Bet:Suc:WFI 2:1:6.4
- Cho:Xyl:WFI 2:1:3

IBV 4 °C

Live Titer (EID50 / ml log10) vs Time (weeks)
- Pro:Sor:WFI 1:1:2.5
- IBV 4/91 Ag

FHV1 Room temp.

TCID50 10log/ml vs Time (weeks)
- Pro:Sor:WFI 1:1:2.5
- Pro:Sor:WFI 1:1:10
- Medium

LIQUID VACCINES OF LIVE ENVELOPED VIRUSES

CROSS-REFERENCE TO RELATED APPLICATIONS

This application is a national stage entry under 35 U.S.C. § 371 of PCT/EP2018/086582, filed on Dec. 21, 2018, which claims priority to EP17210395.4, filed on Dec. 22, 2017, the content of PCT/EP2018/086582 is hereby incorporated by reference in its entirety.

The present invention relates to the field of vaccinology. In particular the invention relates to liquid vaccine compositions of live enveloped viruses. Further the invention relates to methods for the preparation of such compositions, and to their medical uses, to a kit of parts, and to the use of NADES.

Deep eutectic solvents (DES) are well-known compositions that combine a number of remarkable properties. In general these are mixtures of compounds that are liquid at ambient temperatures but have a low water content. Also, the small amount of water that is present is tightly bound, limiting its availability for chemical or biological processes. This is represented by very low water activity values. DES are for example described by Abbott et al., 2003, Chem. Commun., vol. 1, p. 70-71, and in WO 2009/120839.

DES are also called 'protic ionic liquids'. Predecessors are the 'ionic liquids', consisting of only a single molten salt, which are in use since a long time in various industrial applications, for example as solvents for metals, or for extraction of cellulose or biofuels.

Being highly ionic, but at the same time very low in water activity, DES are very effective as solvents for polar hydrophobic compounds. Examples range from the extraction of gasses, minerals, or industrial bulk products, to the solubilisation of pharmaceuticals. DES have also been used for the extraction and stabilisation of biomolecules such as enzymes and RNA, see U.S. Pat. No. 8,247,198 and WO 2011/155829, respectively.

Since about 2011 a special form of DES are being considered, composed of naturally occurring substances. These so-called 'natural DES', or NADES, are described in: Choi et al., 2011, Plant Physiol., vol. 156, p. 1701-1705; and Dai et al. 2013, Anal. Chim. Acta, vol. 766, p. 61-68. NADES currently receive much interest as 'green' solvents, which can be used for the extraction of natural products, and as solvents for use in natural pesticides.

Viruses are important pathogens for humans and animals. Because for most viruses there are either no antiviral drugs, or the use of such drugs is not feasible, therefore the most used defence against viral infections and -disease is by vaccination. Viral vaccines can exist of inactivated (killed) virus, which usually requires an immunological adjuvant to promote an adequate immune response. When applying vaccines comprising 'live' (i.e. replicative) virus, there is usually no need for an adjuvant, because the virus can replicate in the vaccinated host, which causes an immune response. Typically live virus vaccines comprise viruses with attenuated virulence, so as not to induce (serious) disease from the vaccination itself.

Important problem in the vaccine industry is how to preserve the viability of such live attenuated viruses during the process of their production, harvesting, formulation, and shelf-life as finished product. Hardly any virus can survive such treatments and storage for up to 2 years without some sort of stabilisation. Some viruses even require being stored and marketed in liquid nitrogen, which is of course very expensive and laborious. However the most applied method is to remove most of the water from a sample by lyophilisation of the live attenuated virus in an appropriate stabiliser, to form a vaccine consisting of a freeze-dried body, e.g. in the form of a cake or lyosphere. The freeze-dried vaccine, in a protective atmosphere, can be stored for prolonged periods, typically at −20 or at 4° C. Upon vaccination the freeze-dried body is normally dissolved in an appropriate diluent, and the reconstituted virus can be administered to a target in need of such vaccination.

However the process of freeze-drying is laborious, expensive, and extremely time-consuming; e.g. production runs up to 4 or even more days are normal, requiring huge capital investments in freeze-drying equipment. Therefore options have been investigated for providing live virus vaccines in liquid form, see for example WO 2014/029702, WO 2014/140239, and WO 2015/121463. These publications describe aqueous liquids, comprising sugar additives up to 40% w/v, and other components such as buffers and amino acids. However, even these compositions do not always provide the desired longevity for live virus products, especially for sensitive viruses, or in situations where refrigeration is not available or reliable.

Consequently, there is a need in the field for stabilised live virus vaccines that do not need to be produced by freeze-drying, but are sufficiently stable in liquid form with sensitive viruses, and upon prolonged storage.

Virus stability is dependent on several factors, mainly: physical, chemical and biological. Physical factors are mainly temperature and time; chemical factors derive from the composition that the virus is in, including pH, osmolarity, and water content. Biological factors relate to water activity and to the characteristics of the virus itself. Typically the most stable viruses are small, have a DNA genome, and most relevant: do not have a viral envelope.

In general enveloped viruses are the most unstable viruses, especially when they are large and/or comprise an RNA genome. There are several families of stability-sensitive enveloped viruses, and in these families there are many virus species that are of human medical- or of veterinary relevance. These are described in handbooks such as Fields Virology (4th Edition 2001, Lippincott Williams & Wilkins, ISBN-10: 0781718325). Just some examples are Paramyxo-, Herpes-, and Coronaviridea.

In the prior art, WO 2014/029702, WO 2014/140239, and WO 2015/121463 describe liquid vaccine compositions of live viruses, wherein the composition does not comprise a DES, and the liquid comprises at least 60% w/v of water. In these aqueous compositions the water activity ($a_w$) is over 0.85.

WO 2011/155829 describes the extraction of biological materials using NADES. One of the options listed is the extraction of proteinic materials such as vaccines.

Similarly, WO 2014/131906 describes amongst others, a fixative for a virus in blood or tissue, with special focus on the extraction and stabilisation of the viral RNA for clinical diagnostics. The fixative is a DES, and while WO 2014/131906 lists a large number of possible DES compositions, actual use is made only of compositions comprising urea or trifluoroacetamide as the proton-acceptor, and choline or betaine as the proton donor. In WO 2014/131906 the most preferred DES is composed of choline-chloride and trifluoroacetamide, which is therefore not a NADES, and trifluoroacetamide is not an acceptable pharmaceutical excipient.

Byrne et al. (2012, Phys. Chem. Chem. Phys., vol. 14, p. 10119-10121) describe the stabilisation of a plant virus: tobacco mosaic virus (TMV) in a protic ionic liquid. Even though it has an RNA genome, as a plant virus TMV is not enveloped. Further the paper does not disclose a vaccine, and does not provide quantative data on long-term stability of viral infectiveness. Also, the protic ionic liquid employed by Byrne et al. is based on mesylate (methane sulfonate) and ethylammonium and is therefore not a NADES.

It is an object of the present invention to overcome a disadvantage in the prior art, and to accommodate to a need in the field by providing a live virus vaccine that does not need to be produced by freeze-drying, but is sufficiently stable even for sensitive viruses.

Surprisingly it was found that this object can be met, and consequently one or more disadvantages of the prior art can be overcome, by providing a liquid vaccine composition that is able to stabilise sensitive viruses such as enveloped viruses. This is achieved by employing as vaccine carrier a NADES with a water activity below 0.8.

This discovery opens up a number of very favourable applications: stable vaccines can now be made even for sensitive viruses, without the need for freeze-drying, which is a great saving in costs of time, labour, and capital investments. Further, being in liquid form at ambient temperatures, allows easy administration to a target human or animal. Further, the natural compounds allow use as pharmaceutical excipients.

It was unexpected that a DES would be able to stabilise enveloped viruses: as powerful solvents, DES were expected to dissolve the delicate viral envelope and extract the viral proteins and nucleic acids. On the contrary however, NADES formulations have been found to be able to stabilise enveloped viruses. This stabilisation was better than observed for aqueous liquid compositions. For example, in stability studies with live canine para-influenza virus (CPiV), significant viral titres could be maintained for up to 8 weeks at 25° C. in a liquid vaccine composition based on a NADES with very low water activity, whereas the virus stored in complete culture medium was almost undetectable within two weeks.

Also it was surprisingly found that the liquid vaccine composition according to the invention, comprising a NADES was well tolerated upon direct injection into a target animal, and was useful for intranasal administration.

It is not known exactly how or why a NADES is such an effective stabiliser for enveloped live viruses. Although the inventors do not want to be bound by any theory or model that might explain these findings, they speculate that the very low water activity in a DES is responsible for maintaining viral stability, and that the natural origin of the ingredients of a NADES are less aggressive to the sensitive virus than common ingredients of DES.

Therefore in one aspect the invention relates to a liquid vaccine composition comprising a live enveloped virus and a pharmaceutically acceptable carrier, characterized in that the carrier is a natural deep-eutectic solvent (NADES), and the vaccine has a water activity of less than about 0.8.

The term "liquid" is used in its common meaning, referring to a composition that can flow at a certain temperature and in a certain time period. One way to determine liquid properties is a tilt test wherein a container with a composition at a certain temperature is tilted, and when after a certain amount of time any change of form of the composition is detected, that composition is classified as being a liquid.

A "vaccine" is well known to be a composition that has a medical effect. A vaccine comprises an immunologically active component, and a pharmaceutically acceptable carrier. The 'immunologically active component', in the present case: comprises a live virus. The vaccine is recognised by the immune system of the target human or animal, which induces a protective immunological response. The response may originate from the targets' innate- and/or from the acquired immune system, and may be of the cellular- and/or of the humoral type.

A vaccine generally is efficacious in reducing the severity of an infection, for example by reducing the number of the pathogens, or shortening the duration of the pathogen's replication in a host animal.

Also, or possibly as a results thereof, a vaccine generally is effective in reducing or ameliorating the (clinical) symptoms of disease that may be caused by such infection or replication, or by the target's response to that infection or replication.

The term "comprising" (as well as variations such as "comprise", "comprises", and "comprised") as used herein, intends to refer to all elements, and in any possible combination conceivable for the invention, that are covered by or included in the text section, paragraph, claim, etc., in which this term is used, even if such elements or combinations are not explicitly recited; and not to the exclusion of any of such element(s) or combinations.

Thus any such text section, paragraph, claim, etc., can therefore also relate to one or more embodiment(s) wherein the term "comprising" (or its variants) is replaced by terms such as "consist of", "consisting of", or "consist essentially of".

While it is biologically incorrect to refer to a virus as being "live", that is the common way to refer to a virus that is not inactivated. Consequently, for the invention the term "live" refers to a virus that is capable of replication under appropriate conditions, e.g. in suitable host cells.

In practice the live virus comprised in the liquid vaccine composition according to the invention will be of attenuated pathogenicity, such virus is also called 'modified live'.

"Attenuated" for the invention is defined as causing a lower level of lesions, and/or having a reduced rate of infection or of replication, as compared to the unmodified, non-attenuated, or 'wildtype' form of such virus. Attenuation of a virus can be obtained in different ways, for example by passageing and selection through experimental animals or in cell-culture, or via recombinant DNA technology, all well known in the art.

An "enveloped virus" is a well-known type of human- or animal virus having a phospholipid coat. Examples are viruses of: Asfar-, Baculo-, Hepadna-, Herpes-, and Poxvirus families; Corona-, Flavi-, and Togavirus families; Arena-, Bunya-, Filo-, Orthomyxo-, Paramyxo-, Pneumo- and Rhabdovirus families; as well as Reo- and Retrovirus families.

A viral envelope is an element of viruses from several families of human- or animal viruses, and is derived by the virus upon budding from its animal or human host cell. The envelope is a lipid bilayer and comprises phospholipids and proteins. The viral envelope is both very sensitive to damage, as well as critical for the capability of enveloped viruses to infect new host cells. Any damage thus drastically reduces the viral titre as measured by an infectivity index.

Consequently, the stability of a live enveloped virus can effectively be indicated in terms of the infectivity of the virus, i.e. the capability to infect suitable host cells, or a suitable experimental animal. This can be determined in vivo, but more conveniently in vitro, for example using fertilised eggs or a cell-culture of suitable host cells. Virus infectivity can then e.g. be expressed and compared before and after stabilisation, for example as the titre in terms of its tissue culture infective dose (TCID50), plaque forming units, or egg infective dose (EID).

For the invention, a "pharmaceutically acceptable carrier" is a liquid of a high grade of purity and preferably sterile. In the present case the carrier is a NADES. The carrier can comprise further additives, such as stabilisers, anti-oxidants, or preservatives.

A "deep-eutectic solvent" (DES) is well-known in the art as an ionic liquid comprising a mixture of at least two compounds at a molar ratio that forms a eutectic mixture, whereby the eutectic point of the resulting mixture is significantly lower than the melting points of the individual compounds. This reduction of the melting point of the mixture is caused by the interaction of the compounds, one acting as proton donor, and one other acting as proton acceptor, which provides stable hydrogen-bonding without crystallisation, allowing the mixture to be in liquid form at much reduced temperatures, as compared to its constituents. Commonly 'eutectic' means: easy melting.

For the invention, the individual compounds used to form a DES for the invention have melting points above about 80° C., and the DES has a melting point below about 40° C. For example, the melting points of betaine and sucrose are 310° C. and 186° C. respectively, while a NADES formed at a molar ratio for betaine:sucrose of 2:1 with some water included, was found to form a clear liquid that remained fluid even at −20° C.

The term "natural" serves to indicate that the compounds used to form the natural DES (NADES) for the invention, are organic compounds that under normal conditions are present in material from biological sources such as plants or animals, in amounts well above trace amounts. Typically such a natural compounds is, or is derived from, a primary metabolite that is present in a specific material of vegetable or animal origin. As the skilled person will appreciate, the term natural is only used herein to characterise the initial origin of a compound for use in a NADES for the invention, and not to characterise the way the compound being used was actually sourced. Thus the natural compound may also be employed for the invention when obtained via (semi-) synthetic production.

Examples of natural compounds that can be used to form a NADES for the invention, are organic acids, amines, sugars, sugar alcohols, and amino acids.

A further advantageous characteristic of the liquid vaccine composition according to the invention, is that the water that is present in the vaccine is tightly bound in the structure of the NADES. The result of this is that the amount of water that is available for chemical or biological processes that could influence the stability of the enveloped virus, is very limited. This feature is commonly expressed in the value of the water activity, indicated by the symbol: $a_w$. The water activity varies between an upper limit of 1.0 for pure water, and the lower limit of 0. Water activity is commonly measured by comparing (at the same temperature) the vapour pressure of a test composition, relative to that of pure water and to a number of saturated salt-solutions of known water activity. This is described in different handbooks, reviews and manuals, such as for example on the conservation of fruits and vegetables in the FAO agricultural service bulletin no. 149 (Cánovas et al, FAO, Rome, 2003, ISBN 92-5-104861-4); and a review is in 'Fundamentals of water activity', Decagon Devices Inc., Washington, 2015 [Direct-Industry, Decagon Devices Inc/fundamentals-water-activity/64142-634433].

At a water activity less than 0.8 growth of most bacteria is stopped; at less than 0.7 growth of most yeasts and moulds is stopped, and at a water activity less than 0.4 most enzyme activity is effectively stopped.

Equipment and procedures to measure water activity are well known and available, for instance by using headspace pressure analysis.

For the invention, the indicated water activity refers to the water activity of the liquid vaccine composition according to the invention in the form of a final product, for example such as is offered by a commercial producer, and in which form it can be stored for prolonged time. Therefore this refers to the liquid vaccine composition according to the invention before it is diluted in any way (as described herein below), shortly before administration to a target.

For the invention "about" indicates that a number can vary between ±10% around its indicated value. Preferably "about" means±9% around its value, more preferably "about" means±8, 7, 6, 5, 4, 3, 2% around its value, or even "about" means±1% around its value, in that order of preference.

As will be evident to the person skilled in the art of the field of the invention, that within the embodiments disclosed herein for the invention there will be combinations of a certain type of NADES and type of virus that are more favourable than other combinations, for example with regard to the virus' stability. Nevertheless, the skilled person will be capable of selecting, optimizing and fine-tuning combinations and composition according to the present invention, using nothing but routine methods and materials, with the information as disclosed herein. Further details of preferred embodiments and of further aspects of the invention will be described below.

It was found that effective liquid vaccine compositions according to the invention can be prepared with water activities between about 0.8 and about 0.1.

Therefore in an embodiment of the liquid vaccine composition according to the invention, the water activity of the vaccine is less than about 0.7; more preferably less than about 0.6, about 0.5, about 0.4, about 0.3, or even less than about 0.2, in this order of preference.

It was found that the NADES compositions that were most effective and advantageous for use in the liquid vaccine composition according to the invention, were combinations of natural organic compounds selected from (salts of) organic acids, amines, and amino acids, combined with polyols such as sugars and sugar alcohols.

Therefore, in an embodiment of the liquid vaccine composition according to the invention, the NADES comprises an organic salt and a polyol.

In this composition of the NADES for the invention, the organic salt acts as the ionic species which is the proton donor, and the polyol acts as the proton acceptor.

The "organic salt" is a salt of any organic acid or base, including zwitterions, that is within the definition of being a natural compound as presented herein above, and that is capable of forming a deep-eutectic solvent for the invention as described herein. A skilled person is perfectly capable of selecting an organic salt for the present invention, and applying that to form a NADES.

Further the organic salt should be a pharmaceutically acceptable excipient of a vaccine composition. Such vaccine excipients are for example described in governmental regulations such as the European Pharmacopoeia and the American 9 CFR, and in handbooks such as: The Handbook of Pharmaceutical Excipients (R. Rowe et al., Pharmaceutical press 2012, ISBN 0857110276); Remington: the science and practice of pharmacy (2000, Lippincot, USA, ISBN:

683306472), and: "Veterinary vaccinology" (P. Pastoret et al. ed., 1997, Elsevier, Amsterdam, ISBN 0444819681).

In a preferred embodiment of the liquid vaccine composition according to the invention, the organic salt is selected from salts of: betaine, proline, carnitine, and choline.

For the invention, 'betaine' refers to the compound N,N, N-trimethylglycine, CAS nr. 107-43-7, which is also known as glycine-betaine. Proline is CAS nr. 609-36-9. Carnitine is CAS nr. 541-15-1. Choline is CAS nr 62-49-7.

In a preferred embodiment the carnitine is L-carnitine.

In a preferred embodiment the choline is choline-chloride (CAS nr. 67-48-1).

The organic salt for use in the invention can be used as different salts, isomeric forms, hydrate- or anhydrous forms, etcetera. The skilled person is perfectly capable of selecting and testing a suitable form of the organic salt for use in the invention.

The compounds for use in the NADES for the invention are readily available in different purities and qualities from a variety of commercial suppliers. Preferably the compound is used in a pharmaceutical grade quality.

Similarly the water that may be added in the preparation of the NADES for the invention, is preferably a water of high quality and purity, and suitable for parenteral injection, named 'water-for-injection'. Typically this is double distilled water, reverse-osmosis water, or the like. The water will be sterile, and essentially free from pyrogens.

For the invention, a "polyol" is an organic compound containing two or more hydroxyl groups. However, very large polymers that are under the definition of a polyol, such as cellulose, are not effective at forming a NADES as defined herein, thereby they are excluded for use in the invention. Consequently, polyols for use in the invention have a molecular weight of less than about 10.000 grams per Mole. More preferably polyols for use in the invention have a molecular weight of less than 5000, or even less than 1000 grams per Mole, in this order of preference.

Preferred polyols for use in the invention are sugars or sugar-alcohols, as these have demonstrated to be versatile components that allow the generation of a variety of effective NADES compositions for use in the invention.

Therefore in an embodiment of the liquid vaccine composition according to the invention, the polyol is a sugar or a sugar-alcohol.

A "sugar" for the invention is any compound from the group of water-soluble carbohydrates of relatively low molecular weight that typically have a sweet taste. The term "sugar" includes reducing sugars such as fructose and maltose, as well as non-reducing sugars such as sucrose and trehalose. The term sugar covers mono-, di-, or poly-saccharides up to and including hexa-saccharides.

Therefore, in an embodiment of the polyol for use in the liquid vaccine composition according to the invention, the sugar is selected from: fructose, maltose, sucrose, glucose and trehalose.

In a preferred embodiment of the liquid vaccine composition according to the invention, the sugar is sucrose.

The polyol for the invention can also be a sugar alcohol. For the invention "sugar alcohols" are hydrogenated sugars, that comprise 3 or more carbon atoms, and can be based on mono-, di-, or poly-saccharides.

In an embodiment of the polyol for use in the liquid vaccine composition according to the invention, the sugar-alcohol is selected from: glycerol, xylitol, mannitol, and sorbitol.

Glycerol is CAS nr. 56-81-5. Xylitol is CAS nr. 87-99-0. Mannitol is CAS nr. 69-65-8. Sorbitol is CAS nr. 50-70-4.

In a more preferred embodiment the sugar-alcohol is selected from the group of: glycerol, xylitol, and sorbitol.

In an embodiment, the sorbitol is D-sorbitol.

In an even more preferred embodiment of the polyol for use in the liquid vaccine composition according to the invention, the polyol is selected from: sucrose, glycerol, xylitol, and sorbitol.

As also described for the organic salts above, the polyol can be used in different isomeric forms, hydrate- or anhydrous forms, etcetera. The skilled person is perfectly capable of selecting and testing a suitable form of a polyol for use in the invention.

In an embodiment of the NADES for the liquid vaccine composition according to the invention, the organic salt is selected from salts of: betaine, proline, carnitine, and choline; and the polyol is selected from fructose, maltose, sucrose, trehalose, glycerol, xylitol, mannitol, and sorbitol.

In a preferred embodiment of the NADES for the liquid vaccine composition according to the invention, the organic salt is selected from: betaine, proline, and choline; and the polyol is selected from sucrose, glycerol, xylitol, and sorbitol.

In a more preferred embodiment of the NADES for the liquid vaccine composition according to the invention, the organic salt is selected from proline and choline; and the polyol is selected from glycerol, xylitol, and sorbitol.

For the invention, the organic acid and the polyol can be applied in different molar ratios, providing NADES compositions with different properties. These can be optimised by a skilled person to arrive at an optimally stabilising liquid vaccine composition according to the invention.

Therefore, in an embodiment of the liquid vaccine composition according to the invention, the molar ratio between the organic salt and the polyol, as defined herein, is between 1:5 and 5:1.

In a preferred embodiment of the liquid vaccine composition according to the invention, the molar ratio between the organic salt and the polyol, as defined herein, is between 1:4 and 4:1, between 1:3 and 3:1, or even is between 1:2 and 2:1, in this order of preference.

For the invention the indication of a range intends to include the stated end-points.

As described above, the liquid vaccine composition according to the invention can be prepared with a certain water content. By varying this water content, the properties of the vaccine can be optimised, for example in regard of the viscosity of the liquid vaccine composition. Effective NADES with little viscosity can be created with water content up to 50% w/v (Dai et al., 2015, vol. 187, p. 14-19). Higher amounts of water may disturb the network of hydrogen bonds of the NADES.

The lower limit of water content in the liquid vaccine composition according to the invention will be determined by practical factors, such as: how little water can be used for the solubilisation of the compounds to form the NADES, and how much water is required to reach a viscosity of the NADES that is low enough so that it can still be processed or used. Further, an amount of water is introduced into the mixture by the virus composition that is admixed with the NADES, to dissolute the enveloped virus into the mixture, and prepare the liquid vaccine composition according to the invention.

The ratio of the volumes of the NADES and the virus composition to be combined, will typically be higher than 5:1 v/v, e.g. 10:1 v/v or above.

Therefore, in an embodiment of the liquid vaccine composition according to the invention, the water content in the composition is less than about 50% w/v.

Preferably the water content in the liquid vaccine composition according to the invention is less than about 40% w/v, less than about 30, 25, 20, 15, 10, 8, 7, 6, or even less than about 5% w/v, in that order of preference.

More preferably the water content in the liquid vaccine composition according to the invention is between 50 and 0.5% w/v; between 40 and 1% w/v; between 30 and 1.5% w/v; between 20 and 2% w/v; or even between 10 and 3% w/v, in this order of preference. Again, the ranges including their end-points.

The water content is expressed as a percentage of weight per volume "w/v", which is the weight of the water in the liquid vaccine composition according to the invention per unit of volume of the composition. Water content can be measured using different procedures, for example by Karl Fischer titration, well known in the art.

Like for the water activity, the liquid vaccine composition in this context is the vaccine in the form of a final product, before any dilution is applied prior to administration to a target.

As described, the liquid vaccine composition according to the invention is very effective in stabilising the viability of enveloped viruses. This is for example evident from the results of infectivity titrations described herein, that were obtained for different enveloped viruses formulated in the liquid vaccine composition according to the invention, after prolonged storage, even at ambient temperatures.

In an embodiment of the liquid vaccine composition according to the invention, the enveloped virus is selected from the group of virus families of: Asfar-, Baculo-, Hepadna-, Herpes-, Pox-, Corona-, Flavi-, Toga-, Arena-, Bunya-, Filo-, Orthomyxo-, Paramyxo-, Pneumo-, Rhabdo-, Reo- and Retroviruses.

For the invention, the indicated virus families refer to viruses having the characterising features of its taxonomic group-members such as the morphologic, genomic, and biochemical characteristics, as well as the biological characteristics such as physiologic, immunologic, or pathologic behaviour. The same applies for a reference to a viral genus, as well as to a reference to names of individual virus species.

As is known in the field, the classification of a microorganism in a particular taxonomic group is based on a combination of such features. The invention therefore also includes species of virus from the indicated families or from indicated species names, that are sub-classified therefrom in any way, for instance as a subspecies, strain, isolate, genotype, variant, subtype or subgroup and the like.

Further, it will be apparent to a person skilled in the field of the invention that while a particular family, subfamily, genus or species of enveloped virus for the invention may currently be assigned to that group, however that is a taxonomic classification that could change in time as new insights can lead to reclassification into a new or different taxonomic group. However, as this does not change the virus itself, or its antigenic repertoire, but only it's scientific name or classification, such re-classified viruses remain within the scope of the invention.

Samples of enveloped virus for use in the invention can be obtained from a variety of sources, e.g. as field isolate from a human, or from an animal in the wild or on a farm, or from various laboratories, (depository) institutions, or (veterinary) universities.

Particularly sensitive to loss of infectivity titre are enveloped viruses with an RNA genome.

Therefore in an embodiment of the liquid vaccine composition according to the invention, the enveloped virus has an RNA genome.

The RNA genome of the enveloped virus for the invention can be single stranded or double stranded, can be linear or circular, and can be in one piece or can be segmented in two or more pieces.

In a preferred embodiment of the liquid vaccine composition according to the invention, the enveloped virus is selected from the group of virus families with RNA genome of: Corona-, Flavi-, Toga-, Arena-, Bunya-, Filo-, Orthomyxo-, Paramyxo-, Pneumo-, Rhabdo-, Reo- and Retroviruses.

Even more preferred are enveloped viruses with an RNA genome, where the virus is of a relatively large size.

Therefore in a more preferred embodiment of the liquid vaccine composition according to the invention, the enveloped virus with RNA genome is selected from the group of virus families of: Arena-, Filo-, Orthomyxo-, Paramyxo-, Pneumo-, and Rhabdoviruses.

In a more preferred embodiment of the liquid vaccine composition according to the invention, the enveloped virus is selected from the virus families of: Corona-, Pneumo-, and Paramyxoviruses.

It is well within reach of the skilled person to further optimise a liquid vaccine composition according to the invention. Generally this involves the fine-tuning of the efficacy of the vaccine to further improve its provided immune-protection. This can be done by adapting the dose, volume, or antigen content of the vaccine, or by application via a different route, method, or regime. All these are within the scope of the invention.

A liquid vaccine composition according to the invention may additionally comprise other compounds, such as an additional antigen or micro-organism, a cytokine, or an immunostimulatory nucleic acid comprising an unmethylated CpG, etc. Alternatively, the liquid vaccine composition according to the invention, may itself be added to a vaccine.

The liquid vaccine composition according to the invention can advantageously be combined with one or more further antigens, e.g. derived from a micro-organism pathogenic to an intended human or animal target. Such a further antigen may itself be an infectious micro-organism, or be inactivated, or a subunit. The further antigen may consist of a biologic or synthetic molecule such as a protein, a carbohydrate, a lipopolysacharide, a lipid, or a nucleic acid molecule.

The liquid vaccine composition according to the invention may comprise a preservative, such as thimerosal, merthiolate, phenolic compounds, and/or gentamicin. Preferably no preservative is employed.

In an embodiment of the liquid vaccine composition according to the invention, one, or more, or all of the conditions apply, selected from the group consisting of:

- the vaccine has a water activity of less than about 0.8, and comprises a NADES;
- the water activity of the vaccine is less than about 0.7; more preferably less than about 0.6, about 0.5, about 0.4, or even less than about 0.3, in this order of preference;
- the NADES consists of an organic salt and a polyol;
- in the NADES the organic salt is selected from salts of: betaine, proline, carnitine, and choline;
- the carnitine is L-carnitine;
- the choline is choline-chloride;
- the polyol is a sugar or a sugar-alcohol;

the sugar is selected from: fructose, maltose, sucrose, glucose and trehalose;

the sugar-alcohol is selected from: glycerol, xylitol, mannitol, and sorbitol; more preferred the sugar-alcohol is selected from the group of: glycerol, xylitol, and sorbitol;

the sorbitol is D-sorbitol;

the polyol is selected from: sucrose, glycerol, xylitol, and sorbitol;

the organic salt is selected from salts of: betaine, proline, carnitine, and choline; and the polyol is selected from fructose, maltose, sucrose, trehalose, glycerol, xylitol, mannitol, and sorbitol;

preferably the organic salt is selected from: betaine, proline, and choline; and the polyol is selected from sucrose, glycerol, xylitol, and sorbitol; more preferably the organic salt is selected from proline and choline; and the polyol is selected from glycerol, xylitol, and sorbitol;

in the liquid vaccine composition according to the invention, the molar ratio between the organic salt and the polyol, as defined herein, is between 1:4 and 4:1; preferably the molar ratio between the organic salt and the polyol, as defined herein, is between 1:3 and 3:1, or even is between 1:2 and 2:1;

the water content in the liquid vaccine composition according to the invention is less than about 40% w/v, less than about 30, 25, 20, 15, 10, 8, 7, 6, or even 5% w/v, in that order of preference;

the water content in the vaccine is between 50 and 0.5% w/v; between 40 and 1% w/v; between 30 and 1.5% w/v; between 20 and 2% w/v; or even between 10 and 3% w/v, in this order of preference;

the enveloped virus is selected from the group of virus families of: Asfar-, Baculo-, Hepadna-, Herpes-, Pox-, Corona-, Flavi, Toga-, Arena-, Bunya-, Filo-, Orthomyxo-, Paramyxo-, Rhabdo-, Reo- and Retroviruses;

the enveloped virus has an RNA genome;

the enveloped virus with RNA genome is selected from the group of virus families of: Corona-, Flavi, Toga-, Arena-, Bunya-, Filo-, Orthomyxo, Paramyxo-, Pneumo-, Rhabdo-, Reo- and Retroviruses; preferably the enveloped virus with RNA genome is selected from the group of virus families of: Arena-, Filo-, Orthomyxo, Paramyxo-, Pneumo-, and Rhabdoviruses; more preferably the enveloped virus with RNA genome is selected from the virus families of: Corona-, Pneumo-, and Paramyxoviruses; and the liquid vaccine composition according to the invention may comprise a preservative, such as thimerosal, merthiolate, phenolic compounds, and/or gentamicin. Preferably no preservative is employed.

As described, the liquid vaccine composition according to the invention can be produced using common techniques and materials. Details and examples of such a method, a use, or a process for preparing a liquid vaccine composition according to the invention, are described herein, and such procedures are readily applicable by a person skilled in the art using routine materials and methods.

For example, the NADES for the invention can be produced at industrial scale, and is then formulated into a vaccine by admixing with a preparation of enveloped virus that was produced in vivo or preferably in vitro. The mixture is then filled-out into appropriately sized containers. The various stages of the manufacturing process will be monitored by adequate tests, for instance by immunological tests for the quality and quantity of the antigens; by microbiological tests for sterility, and absence of extraneous agents; and ultimately by vaccination-studies in animals for confirming efficacy and safety. After completion of the testing for quality, quantity and sterility the vaccine product can be released for sale.

All these are well known to a skilled person, and general techniques and considerations that apply to the preparation of vaccines under well-known standards for pharmaceutical production are described for instance in governmental directives and regulations (Pharmacopoeia, 9CFR) and in well-known handbooks (Pastoret, Lippincot, supra).

Therefore in a further aspect the invention relates to a method for the preparation of the liquid vaccine composition according to the invention, the method comprising the steps of:

a. preparing the NADES, and b. admixing the NADES and a composition comprising the live enveloped viruses.

Conveniently the two steps of the method according to the invention can be performed separated in time and/or in place, with intervening storage, transport, or even further steps. This will allow flexibility in planning and logistics of operation.

The preparation of the NADES for use in the method according to the invention can be done using routine tools and methods. One convenient way is to apply heating of the combined compounds to a temperature that allows them to mix and solubilise, but that does not damage them, e.g. up to about 80° C. The heating can e.g. be done in combination with stirring or with sonification.

Also, one of the components to form the NADES can initially be dissolved in water in more or less concentrated form, after which it can be mixed with (a) further component(s) to form the NADES for the invention, by evaporating off the surplus of water.

The composition comprising the live enveloped virus for use in the method according to the invention can conveniently be derived in different ways, advantageously from an in vitro culture of the virus on a suitable cell-line. Virus-cell cultures can be made at any desired size or volume, up to several 1000 litres in large scale industrial size fermenters applying automated controls and monitoring techniques.

The virus is then harvested from the culture in a way that depends on the characteristics of the virus: as the supernatant, the cell-pellet, or as a whole culture. The virus composition for use in the invention can be prepared using further process steps such as concentration, e.g. using passage over ultra-filtration membranes. The virus composition is then checked for viability and quantity. All this is well-known to a skilled person.

The admixing of the NADES and the virus composition in the method according to the invention, is preferably done using aseptic techniques.

The order and the way of admixing is not critical, in that the NADES may be added to the virus composition, or the other way around. Preferably any mechanical mixing used will be low speed, and low impact. Further, the mixing and/or filling can be done in a protective atmosphere to reduce oxygen exposure.

Convenient equipment for mixing and filling viscous liquids is available from a variety of suppliers of process-equipment.

The present invention for the first time discloses the use of a NADES as described herein, as a carrier for a vaccine intended for a human or animal target.

Therefore, in a further aspect the invention relates to the use of a NADES as described for the invention, as a pharmaceutically acceptable carrier for a vaccine intended for a human or animal target.

Preferably, the use of the NADES according to the invention is as a carrier for a vaccine of an enveloped virus as described herein.

Therefore, in a preferred embodiment of the use of a NADES according to the invention, the vaccine is a liquid vaccine composition according to the invention.

The liquid vaccine composition according to the invention can be administered to a human or animal in the form in which it is supplied for example by a pharmaceutical manufacturer. However, depending on the specific composition of a particular embodiment of the liquid vaccine composition according to the invention, it may be favourable to make a dilution of the liquid vaccine composition. This may facilitate the actual administration to a target for example by reducing the viscosity, or may reduce local reactions upon vaccination of a target.

The diluent for such dilution will typically be a liquid and may be provided separate from the liquid vaccine composition according to the invention. Preferably, the diluent is provided together with the liquid vaccine composition according to the invention, e.g. as a kit of parts.

Therefore in a further aspect, the invention relates to a kit of parts, comprising at least two containers: one container comprising the liquid vaccine composition according to the invention, and one container comprising a liquid diluent.

A “liquid diluent” for diluting the liquid vaccine composition according to the invention, e.g. for inclusion in the kit of parts according to the invention, is a liquid that is suitable for diluting the liquid vaccine composition according to the invention. The liquid diluent can therefore be aqueous, such as water or a buffer. However, because of the low water content of a liquid vaccine composition according to the invention, the diluent can also be oily, or can be an emulsion of oil and water.

In one embodiment the liquid diluent may itself be a liquid vaccine composition, for example a reconstituted freeze-dried live vaccine, or an emulsion-adjuvated inactivated vaccine.

The choice of liquid diluent for diluting the liquid vaccine composition according to the invention, e.g. for inclusion in the kit of parts according to the invention, will depend on several factors, such as: the intended use of the vaccine after it is diluted; the enveloped virus that it comprises; the intended human or animal target for the vaccination; etcetera. A skilled person is perfectly capable of selecting, preparing and applying such a diluent.

The liquid vaccine composition according to the invention can be used either as a prophylactic- or as a therapeutic treatment, or both.

The liquid vaccine composition according to the invention can serve as an effective priming vaccination, which can later be followed and amplified by a booster vaccination, with the same or with a different vaccine.

The liquid vaccine composition according to the invention comprises an amount of live enveloped virus that is immunologically effective.

A skilled person in the field of the invention will be more than capable of determining and optimising such immunologically effective amount of live enveloped virus in a liquid vaccine composition according to the invention, e.g. by monitoring the immunological response following vaccination, or (in the case of an animal target) after a challenge infection, e.g. by monitoring the targets’ signs of disease, clinical scores, or by re-isolation of the pathogen, and comparing these results to a vaccination-challenge response seen in mock-vaccinated animals.

Ways to determine the amount of live virus in a vaccine dose are well-known in the art, and will typically employ techniques of viral titration such as plaque assays, titration in eggs, or animals, or in micro-titration plates. Consequently such a viral infectivity titre can be expressed e.g. in TCID50, EID50, or plaque forming units (pfu).

The targets for the liquid vaccine composition according to the invention are humans or animals in need of a vaccination against infection or disease caused by a pathogenic form of the particular live enveloped virus that is comprised in the vaccine. The age, weight, sex, immunological status, and other parameters of the target to be vaccinated are not critical, although it is favourable to vaccinate healthy, uninfected targets, and to vaccinate as early as possible to prevent any field infection.

The liquid vaccine composition according to the invention, or the liquid vaccine composition that can be prepared by the method according to the invention, or the liquid vaccine composition in diluted form as can be prepared e.g. using the kit of parts according to the invention, is intended for administration to a human or animal target in need of such vaccination. The vaccination induces active immunisation in order to reduce infection and/or of signs of disease caused by a non-attenuated counterpart of the live enveloped virus for the invention. Such reduction of infection refers to preventing or reducing the establishment or the proliferation of a productive infection by the enveloped virus. This is achieved for example by reducing the viral load in the target or shortening the duration of the viral replication. In turn this leads in the target human or animal to a reduction of the number, the intensity, or the severity of lesions and consequential clinical signs of disease caused by the viral infection. Such a vaccine is colloquially referred to as a: vaccine ‘against’ the particular virus, or as a ‘virus vaccine’.

Therefore in a further aspect, the invention relates to a liquid vaccine composition according to the invention for use in the protection of a human or animal target against infection and/or disease caused by a pathogenic form of the live enveloped viruses that are comprised in said vaccine.

In a further aspect the invention relates to a method for the vaccination of a human or animal target, the method comprising the administration of a liquid vaccine composition according to the invention, or of a vaccine as obtainable by the method according to the invention, or by the use of the kit of parts according to the invention.

The liquid vaccine composition according to the invention can be employed for direct administration to a human or animal target according to a method of vaccination according to the invention.

Alternatively, the liquid vaccine composition according to the invention can be administered to a human or animal target in a diluted form. This embodiment of a method of vaccination according to the invention, may facilitate the handling and administration by injection because of its reduced viscosity. Alternatively, or additionally, the administration in diluted form may reduce local reactions in the human or animal target, for example resulting from tissue irritation at the site of inoculation.

Vaccination according to the method of the invention can be performed by parenteral route, i.e. through the skin, e.g.: intramuscular, intraperitoneal, intradermal, submucosal, or subcutaneous. Preferred route of parenteral administration of the liquid vaccine composition according to the invention is by intramuscular or by subcutaneous injection.

Further the liquid vaccine according to the invention can be administered by enteral or mucosal route, i.e. via eye drop, nose drop, oral, enteric, oro-nasal drop, spray, etcetera.

Alternatively, the liquid vaccine composition according to the invention can be administered via a method of mass administration, such a via drinking water, coarse spray, atomisatation, on-feed, etcetera.

It goes without saying that the optimal route of administration of a liquid vaccine composition according to the invention will depend on the specifics of the vaccine that is used, and on the particular characteristics of the target. A skilled person is perfectly capable of selecting and optimising such route and method of administration.

The liquid vaccine composition according to the invention, can be administered by parenteral route in a volume that is acceptable for the target human or animal, and can for instance be at a volume of between about 0.1 and about 10 ml. Preferably one dose is a volume between about 0.1 and about 5 ml, more preferably one dose is between 0.2 and 3 ml.

When administered by intramuscular route, the volume of one dose is preferably between about 0.5 and about 3 ml, more preferably between about 1 and about 2 ml.

When administered by intradermal route, the volume of one dose is preferably between about 0.1 and about 0.5 ml, more preferably about 0.2 ml.

The method, timing, and volume of the administration of a liquid vaccine composition according to the invention is preferably integrated into existing vaccination schedules of other vaccines that the target human or animal may require, in order to reduce stress to the target and to reduce labour costs. These other vaccines can be administered in a simultaneous, concurrent or sequential fashion, in a manner compatible with their registered use.

The invention will now be further described by the following, non-limiting, examples.

EXAMPLES

Example 1: Methods and Materials 1.1 Preparing the NADES Formulations

NADES can be prepared by mixing, which can be accelerated by heating and/or addition of a small amount of water. Some of the samples of NADES as further tested and described herein below were prepared by dissolving organic salts and polyols in an excess of water. Next, the excess of water was removed by rotational evaporation in a waterbath at 70° C. for several hours under reduced atmospheric pressure. The amount of water present in the NADES was calculated by taking into account the weight-loss due to the evaporation.

Other samples of NADES were prepared by sonification method in a waterbath. The required quantities of powders were added to a flask. The flask was briefly shaken or vortexed, to mix the powders. Next the required amount of water was added. This mixture was placed in a sonication-waterbath, set at 45° C., with sonication up to several hours, until a NADES was formed. During sonication temperatures of up to 70° C. could be reached.

1.2 Measurements of Water Activity

Samples

For biological containment purposes the water activities were measured of samples of NADES preparations, so without live virus. However, when knowing the amount of aqueous virus composition that will be added to the NADES to form the liquid vaccine composition according to the invention, the resulting water activity of the combination of NADES and virus composition can be calculated according to Dai et al. (2015, Food Chem., vol. 187, p. 14-19).

Sample Preparation

An amount of NADES sample was transferred to a 10 ml glass vial in order to reach a fill height of approx. ¼ of the vial. For each sample coded vials were filled in duplicate. The vials were closed using an aluminium crimp cap with PTFE stopper, and were placed at room temperature for 12 hours to reach an equilibrium between sample and headspace.

Equipment

The moisture vapour pressure in the headspace of the samples was determined using the Lighthouse FMS-1400 Moisture/Pressure analyser. The samples are inserted into the sample chamber as such. Before sample measurement the system is calibrated using calibration headspace pressure standards in the range of 0-0.2 $a_w$. Also, saturated salt standards were used to calibrate and recalculate the non-linear range from 0.2-1 $a_w$.

Calibration

To calibrate the machine over the full range from $a_w$ 0-1, and to create a reference line of water activity values, a number of standard samples were measured: next to pure water 5 samples of specific saturated salt-solutions were used, and for each of the 6 standards 2 samples were measured in 3 fold. By setting the measured value for pure water to 1.000, the other standard values were determined at $a_w$ of: 0.8511, 0.7547, 0.5438, 0.3307, and 0.1131. Also a series of certified vapour pressure standards were measured.

Results of $a_w$ measurements are included in Table 1.

1.3 Virus Compositions Used for Stability Assays

The viruses used for stability incubation were:

- canine parainfluenza virus (CPiV); from the Paramyxoviridae family
- bovine respiratory syncytial virus (BRSV); also known as the species: bovine orthopneumovirus; from the Pneumoviridae family, Orthopneumovirus genus, and
- bovine parainfluenza 3 virus (PI3); from the Paramyxoviridae family.

All these viruses are enveloped viruses, and have an RNA genome.

1.4 NADES Compositions Used for Stability Assays

NADES compositions used for the stability assays were:

NADES 1: betaine:sucrose:water, in 2:1:6,4 molar ratio

NADES 2: carnitine:glycerol:water, in 2:1:4 molar ration, and

NADES 3: proline:sorbitol:water, in 2:1:5,7 molar ratio.

1.5 Mixing NADES and Virus Compositions

NADES preparations were blended 9:1 v/v with virus compositions in a laminar flow cabinet. To prevent osmotic shock, stabilizer was added gradually and portion-wise to the cooled virus solution. Samples were gently stirred using a sterile magnetic stirring. Care was taken not to entrap air bubbles into the mixture. The mixtures were stored at 2-8° C. until the start of filling into appropriate containers.

Filling the NADES/virus mixture into 3 ml vials was performed in a laminar flow cabinet at 2 ml per vial using a pipetboy, samples were kept on ice. Duplicate samples were prepared for each stability time-point. Also NADES samples without virus were included as negative controls. After filling, vials were capped with an aluminium cap. Samples were then stored at their stability-incubation temperatures.

1.6 Stability Assays

For a number of enveloped viruses, comprised in liquid vaccine compositions according to the invention, extended stability assays were performed. These were done at three temperatures: 4, 15, and 25° C., and during incubation for 1, 2, 4, or 8 weeks. Day zero samples were set apart.

At the appropriate time points, NADES/virus mixtures were taken and used to determine the remaining virus titres, by titration on cells.

Virus titrations were done on 96 well microtitration plates. Proper positive and negative controls were included. Titres were calculated from at least two readings of a sample, using the method of Spearman and Kärber via a computer program, and were expressed in Log 10 TCID50/ml.

CPI virus was titrated on Vero cells, cultured in standard culture medium with 5% FCS and antibiotics. 2×10ˆ5 cells/ml were seeded, and 1:10 dilutions were made on the plates.

Next, the microtiter plates were incubated for 7 days at 37° C. and 5% $CO_2$. Each well was then inspected for cpe as evaluated by lightmicroscopy.

To quantify the amount of infectious BRSV or PI3 in samples, serial tenfold dilutions of test samples were made in standard cell-culture medium and were pipetted into microtitration plates that were pre-seeded with Madin Darby Bovine Kidney (MDBK) cells. After an incubation period of 5-7 days for BRSV, or 4-6 days for PI3, at 37° C. in a humidified 5% $CO_2$ atmosphere, the monolayers were examined for the presence or absence of virus. The plates were fixated and an immune-peroxidase monolayer assay was performed, using a peroxidase-labelled virus-specific monoclonal antibody, in combination with an enzyme-substrate. Detection was done by registering the presence of a coloured precipitate visually.

Results of the stability assays are described in Example 3.

Example 2: Examples of NADES for Use in the Invention

A large number of NADES formulations were prepared for use in the invention, with different compounds, with different molar ratios, and with different water contents.

Table 1 below list a number of the most effective NADES formulations; these yielded clear liquid solutions, that were fluid at room temperature (20-25° C.). Details on their composition and water content are provided. For several of the samples prepared, the water activity was determined and the results are included. Not indicated: the molecular weight of water is 18 Da; trehalose was used as dihydrate.

A number of observations could be made:

- choline, betaine, and proline were the most versatile and effective organic acids for use in the invention, and sorbitol, glycerol, and xylitol were the most effective polyols.
- NADES with water contents up to 37% w/v could readily be made, resulting in liquids of low viscosity
- water activities were generally found to be very low, often below 0.3, and even below 0.1 $a_w$.
- although sugars and amines can react via the Maillard reaction, it was observed that the majority of the prepared NADES remained colourless and visually unchanged after several hours of heating up to 70° C.
- several samples were also fluid at refrigerated conditions of 2-8° C. or even at −20° C.

TABLE 1

NADES liquid at room temperature

| | | | | | | | NADES | | | | | |
|---|---|---|---|---|---|---|---|---|---|---|---|---|
| Organic salt | | | Polyol | | | Water | molar ratio | | | total | water content | water activity |
| compound | Mw | grams | compound | Mw | grams | grams | (organ. salt:polyol:water) | | | (g) | (% w/v) | ($a_w$) |
| Proline | 115 | 17.26 | D-sorbitol | 182 | 27.36 | 5.40 | 1 | 1 | 2 | 50.01 | 10.79% | 0.299 |
| | | 11.27 | | | 35.27 | 3.51 | 1 | 2 | 2 | 50.12 | 7.00% | |
| | | 232.75 | | | 184.14 | 82.69 | 2 | 1 | 4.5 | 499.58 | 16.43% | 0.307 |
| | | 307.03 | | | 242.86 | 311.96 | 2 | 1 | 13.7 | 861.85 | 37.44% | 0.101 |
| | | 20.20 | xylitol | 152 | 26.64 | 3.15 | 1 | 1 | 1 | 49.99 | 6.29% | 0.300 |
| | | 18.98 | | | 25.08 | 5.94 | 1 | 1 | 2 | 50.01 | 11.88% | |
| | | 18.14 | glycerol | 92 | 29.02 | 2.89 | 1 | 2 | 1 | 50.2 | 5.76% | 0.119 |
| Betaine | 117 | 17.49 | D-sorbitol | 182 | 27.18 | 5.35 | 1 | 1 | 2 | 50.02 | 10.69% | 0.238 |
| | | 18.47 | | | 28.72 | 2.90 | 1 | 1 | 1 | 50.09 | 5.80% | |
| | | 19.18 | xylitol | 152 | 24.91 | 5.91 | 1 | 1 | 2 | 50.01 | 11.82% | 0.227 |
| | | 25.78 | glycerol | 92 | 20.26 | 3.95 | 1 | 1 | 1 | 49.99 | 7.90% | |
| | | 18.34 | | | 28.88 | 2.81 | 1 | 2 | 1 | 50.03 | 5.61% | 0.089 |
| | | 5.86 | trehalose | 378 | 8.56 | 4.00 | 2 | 1 | 9.8 | 18.42 | 21.72% | |
| | | | sucrose | 342 | | | 4 | 1 | 13.6 | | | |
| | | 696.11 | | | 1016.97 | 335.65 | 2 | 1 | 6.3 | 2048.73 | 16.45% | 0.391 |
| Choline-Cl | 140 | 20.53 | D-sorbitol | 182 | 26.82 | 2.65 | 1 | 1 | 1 | 50 | 5.30% | 0.097 |
| | | 19.54 | | | 25.47 | 5.10 | 1 | 1 | 2 | 50.11 | 10.17% | |
| | | 22.56 | xylitol | 152 | 24.56 | 2.90 | 1 | 1 | 1 | 50.03 | 5.80% | |
| | | 21.30 | | | 23.21 | 5.48 | 1 | 1 | 2 | 49.99 | 10.96% | |
| | | 1396.2 | | | 760.75 | 271.23 | 2 | 1 | 3 | 2428.18 | 11.13% | 0.174 |
| | | 29.88 | | | 16.28 | 3.87 | 2 | 1 | 2 | 50.03 | 7.74% | 0.109 |
| | | 20.63 | glycerol | 92 | 26.94 | 2.66 | 1 | 2 | 1 | 50.22 | 5.29% | |
| | | 27.94 | | | 18.45 | 3.60 | 1 | 1 | 1 | 50 | 7.20% | 0.091 |
| L-Carnitine | 161.2 | 88.50 | glycerol | 92 | 25.28 | 19.78 | 2 | 1 | 4 | 133.56 | 14.81% | |
| | | 8.06 | trehalose | 378 | 8.56 | 6.00 | 2 | 1 | 14.7 | 22.62 | 26.53% | |

Example 3: Results of Viral Stability Assays

For a number of enveloped viruses, comprised in liquid vaccine compositions according to the invention, extended stability assays were performed, as described above. These were done at three temperatures: 4, 14, and 25° C.

The incubation at 25° C. for 8 weeks can serve as an expedited stability test, indicative of the effect of incubation for 1-2 years at 4° C. This is thus a very severe attack on the virus' stability, and not all samples were expected to survive that long under those conditions.

TABLE 2

Stability results of BRSV and PI3 viruses

| Virus | Temp. | Stabilizer | Duration (weeks) 0 | 1 | 2 | 4 |
|---|---|---|---|---|---|---|
| BRSV | 4° C. | Medium Control | 6.25 | 6.15 | 5.85 | 5.85 |
| | | NADES 1 | 6.25 | 6.10 | 6.05 | 6.15 |
| | | NADES 2 | 6.45 | 6.15 | 6.55 | 6.35 |
| | | NADES 3 | 6.35 | 6.05 | 6.20 | 6.15 |
| | 14° C. | Medium Control | 6.25 | 6.00 | 5.40 | 4.30 |
| | | NADES 1 | 6.25 | 5.85 | 5.75 | 5.65 |
| | | NADES 2 | 6.45 | 5.80 | 5.55 | 4.90 |
| | | NADES 3 | 6.35 | 5.70 | 5.60 | 5.25 |
| | 25° C. | Medium Control | 6.25 | 2.45 | 0.00 | 0.00 |
| | | NADES 1 | 6.25 | 5.10 | 4.10 | 2.45 |
| | | NADES 2 | 6.45 | 2.30 | 0.00 | 0.00 |
| | | NADES 3 | 6.35 | 4.10 | 2.55 | 0.00 |
| PI3 | 4° C. | Medium Control | 6.35 | 5.70 | 5.70 | 5.75 |
| | | NADES 1 | 6.10 | 6.00 | 6.15 | 6.05 |
| | | NADES 2 | 4.55 | 3.95 | 4.00 | 3.60 |
| | | NADES 3 | 5.45 | 5.15 | 4.95 | 5.00 |
| | 14° C. | Medium Control | 6.35 | 5.95 | 5.55 | 5.15 |
| | | NADES 1 | 6.10 | 5.40 | 5.15 | 4.55 |
| | | NADES 2 | 4.55 | 3.30 | 2.90 | 0.00 |
| | | NADES 3 | 5.45 | 4.15 | 3.70 | 0.00 |
| | 25° C. | Medium Control | 6.35 | 4.50 | 2.65 | 0.00 |
| | | NADES 1 | 6.10 | 3.35 | 2.40 | 0.00 |
| | | NADES 2 | 4.55 | 0.00 | 0.00 | 0.00 |
| | | NADES 3 | 5.45 | 0.00 | 0.00 | 0.00 |

TABLE 3

Stability results of CPiV

| CPiV | Temp | Duration (weeks) 0 | 1 | 2 | 4 | 8 |
|---|---|---|---|---|---|---|
| PBS control | 4° C. | 8.85 | 8.20 | 8.20 | 7.91 | 8.15 |
| | 14° C. | | 7.50 | 7.25 | 6.25 | 5.80 |
| | 25° C. | | 6.10 | 3.90 | 2.50 | — |
| NADES 1 | 4° C. | 8.55 | 8.45 | 8.40 | 8.25 | 7.90 |
| betaine:sucrose:water | 14° C. | | 8.25 | 7.85 | 7.30 | 6.40 |
| 2:1:6.4 | 25° C. | | 6.70 | 4.95 | 2.90 | — |
| NADES 2 | 4° C. | 8.60 | 8.40 | 8.45 | 8.30 | 8.40 |
| carnitine:glycerol:water | 14° C. | | 8.25 | 7.95 | 7.45 | 6.85 |
| 2:1:4.0 | 25° C. | | 4.90 | 3.50 | 3.50 | — |
| NADES 3 | 4° C. | 8.65 | 8.55 | 8.50 | 8.55 | 8.25 |
| proline:sorbitol:water | 14° C. | | 8.30 | 8.40 | 8.19 | 7.95 |
| 2:1:5.7 | 25° C. | | 8.15 | 7.75 | 7.35 | 6.10 |

Some Conclusions from the Stability Results

Especially CPiV virus could be stabilised very well by NADES 3 (stab. 3) formulation; even after 8 weeks at 25° C., most of the virus remained infectious.

Similar results were seen for BRSV and PI3 in NADES 1, up to 4 weeks at 25° C.

In general, the liquid vaccine compositions according to the invention, in different compositions for the various enveloped viruses, show remarkable capabilities of stabilisation.

This overcomes the need for lyophilisation, a great economic benefit. Also the liquid nature of the vaccines facilitates administration to human or animal targets.

Example 4: Long Term Stability Assay Results

The experiments described in the Examples 1-3 above were continued over time, and regular samples were taken and measured.

BRSV:

The stability assays were continued with the Pneumovirus BRSV in liquid vaccine compositions based on NADES 1 (Betaine:Sucrose:Water for injection, at 2:1:6.4 molar ratio), NADES 3 (Proline:Sorbitol:WFI, at 2:1:5.7), or NADES 4 (Choline:Xylitol:WFI, at 2:1:3).

Figure 4:
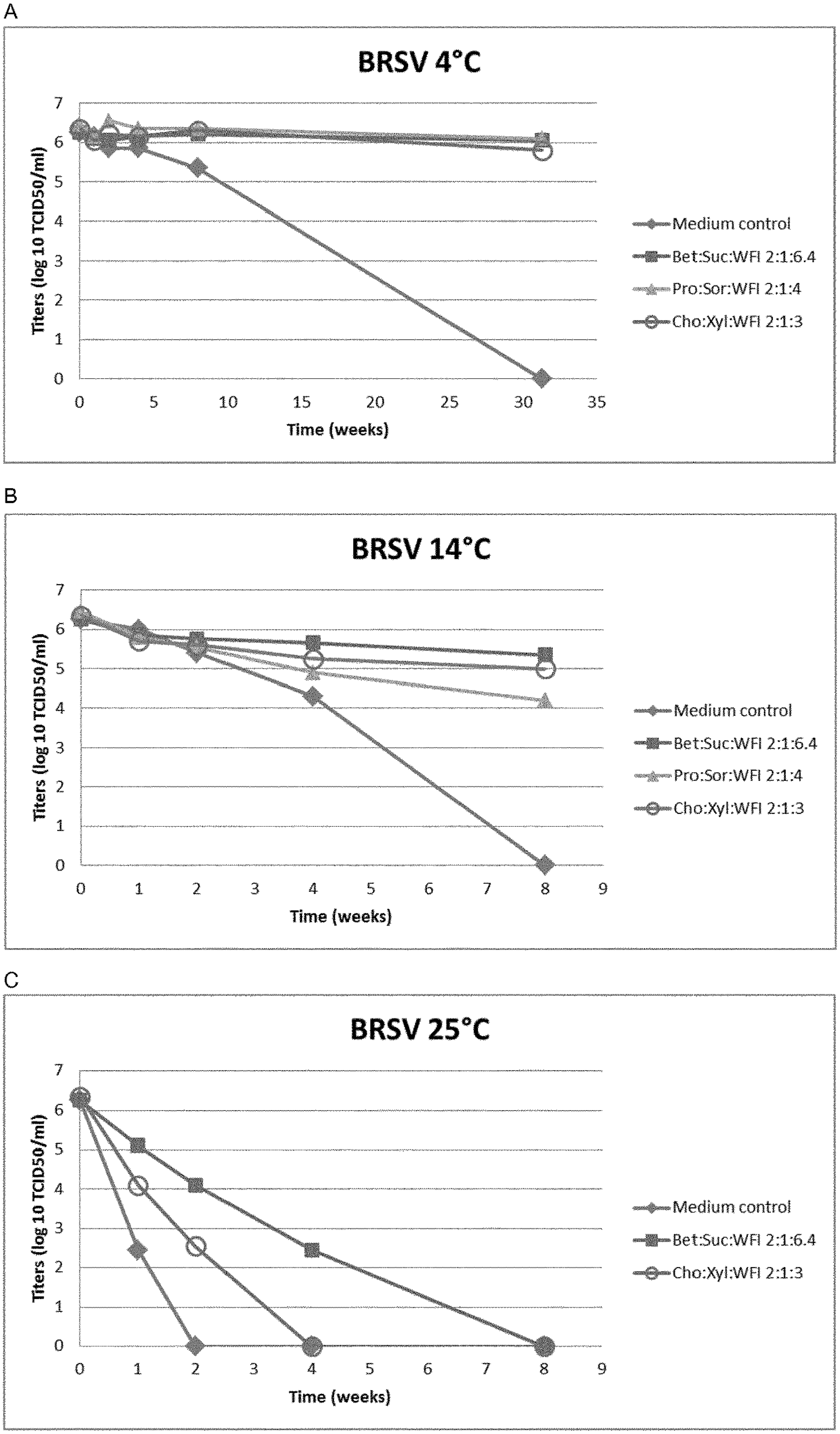

Results are presented in FIG. 4, panels A-C, of continued storage at temperatures of 4, 14, or 28° C., and for 30, 8 or 8 weeks respectively. These are the extensions of the results as depicted in FIG. 1, panels A-C.

It is clear is that liquid vaccine compositions based on all NADES tested (1, 2, and 4), provide a solid stabilising effect to the Pneumovirus BRSV, upon storage at 4 or at 14° C., see FIGS. 4A and 4B. Also, even at the very demanding temperature of 25° C., FIG. 4C, there is a significant stabilisation by NADES 4 and an even better stabilisation by NADES 1.

Further results on BRSV are presented in Example 5

Figure 2:
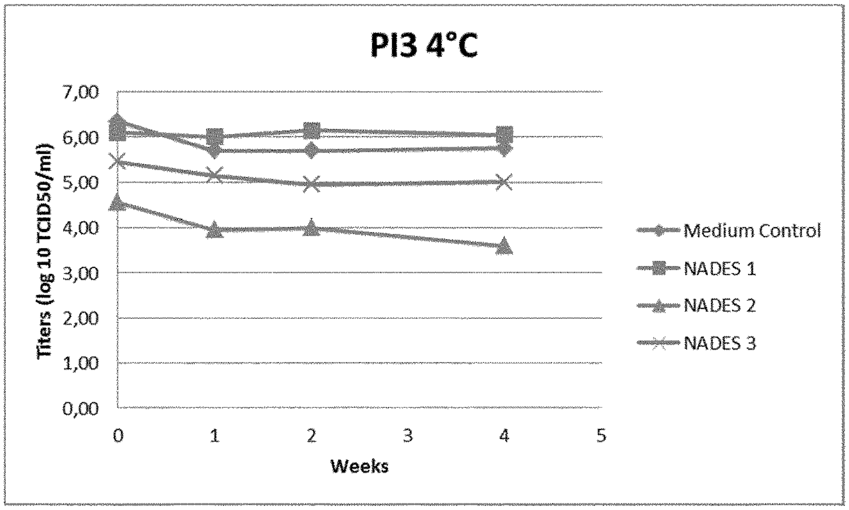
Figure 2:
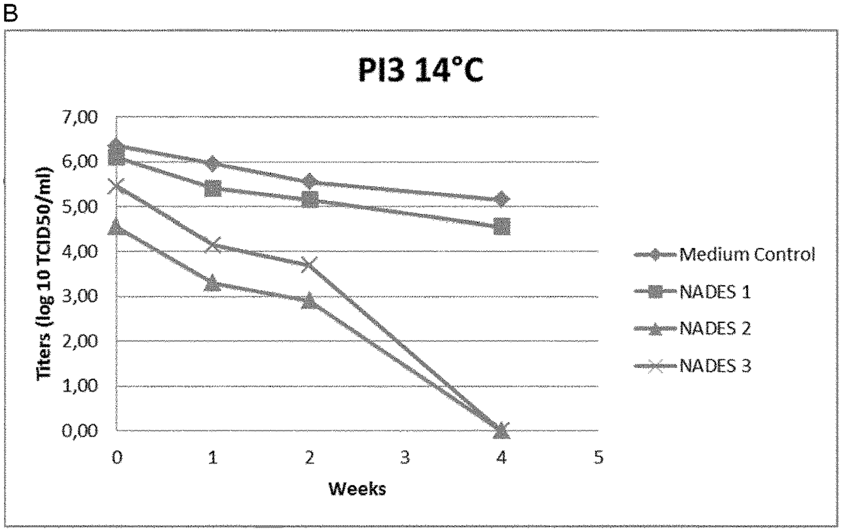
Figure 2:
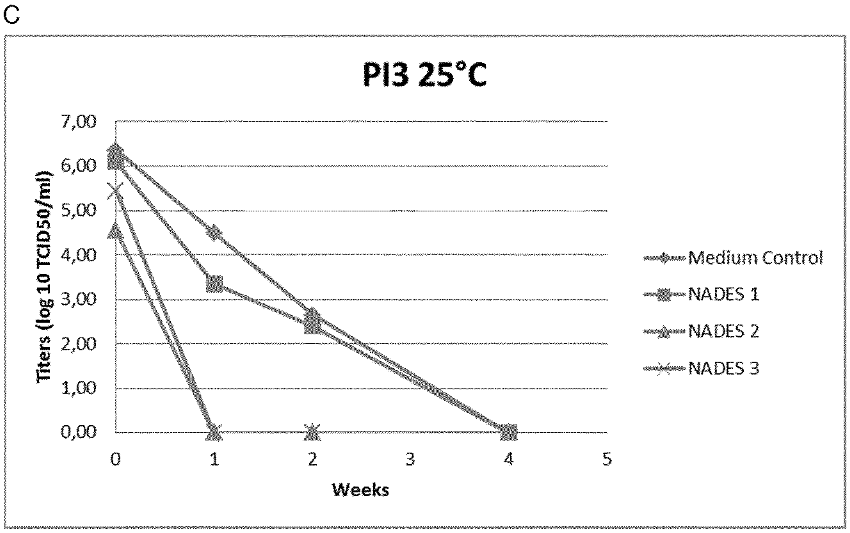
Figure 3:
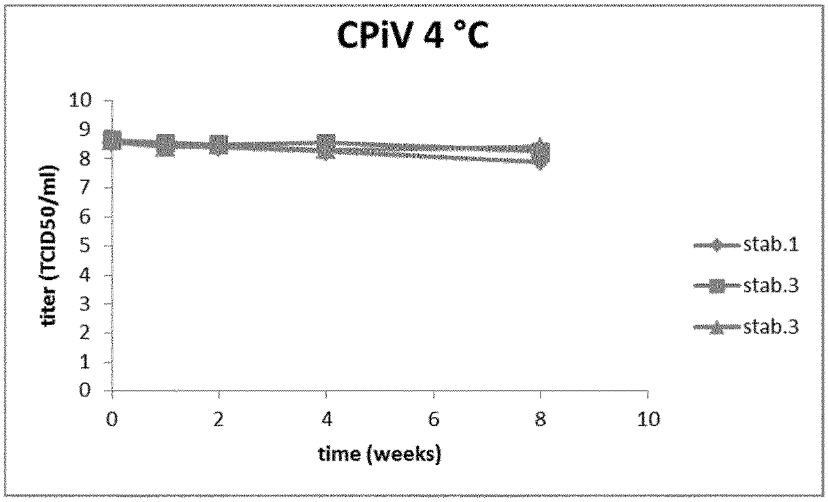
Figure 3:
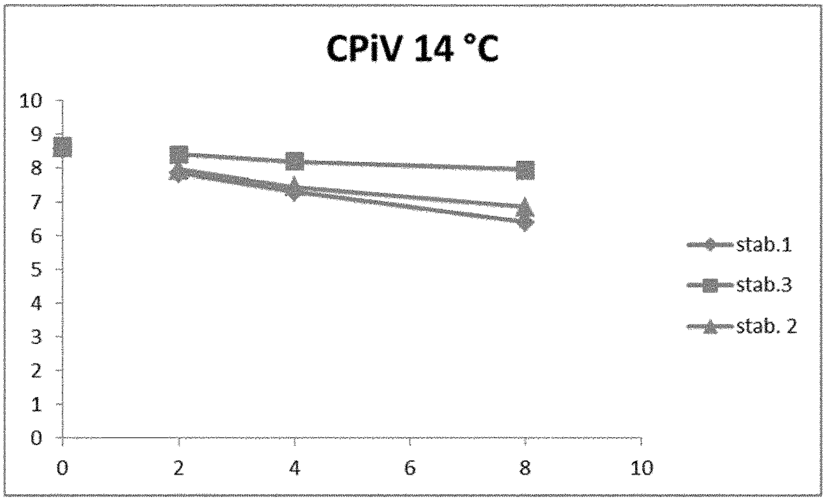
Figure 3:
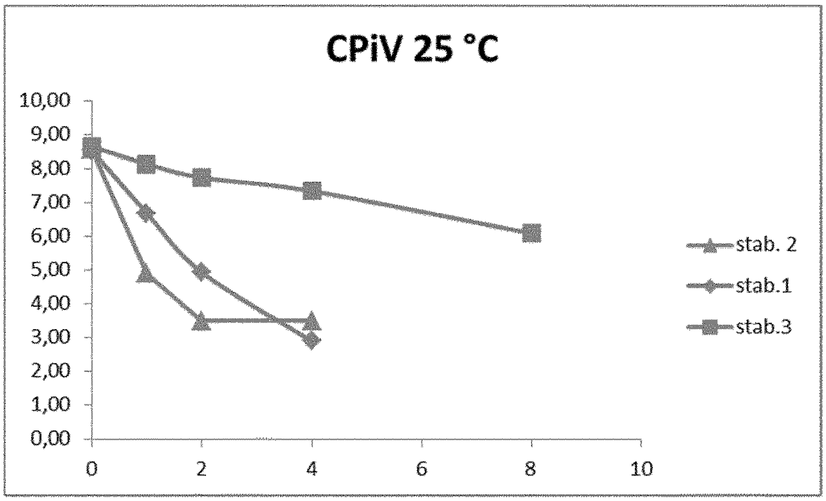
Figure 5:
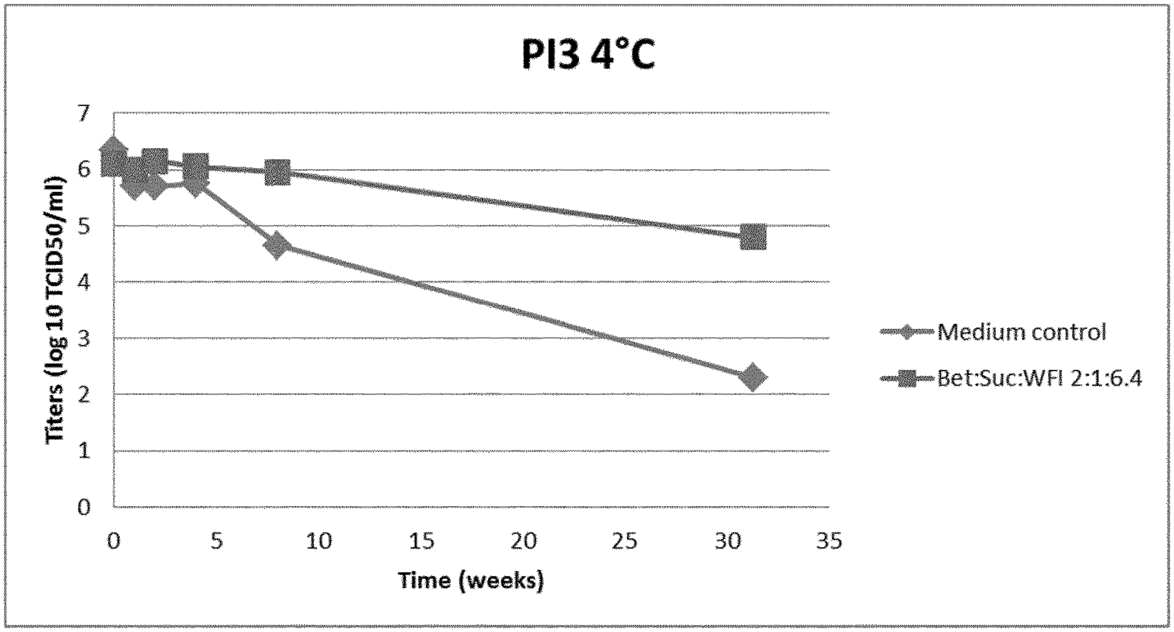

PI3:

For the Paramyxovirus PI3, all liquid vaccine compositions based on NADES 1, 2, or 3, provided some level of stabilisation, see FIG. 2, panels A-C, but the best stabilisation over time was obtained in NADES 1 (Betaine:Sucrose: Water for injection, at 2:1:6.4 molar ratio), as is depicted in FIG. 5: this composition was able to prevent the drop in live viral titre to little more than 1 Log 10, over a period of over 30 weeks at 4° C. In comparison, the control sample in standard culture medium showed a drop in titre of 4 Log 10 over the same period.

CPiV:

The Paramyxovirus CPiV was mixed into liquid vaccine compositions comprising two variants of the Proline:Sorbitol:WFI NADES 3 formulation: NADES 3A and NADES 3B; details are provided in Table 4 below.

Figure 6:
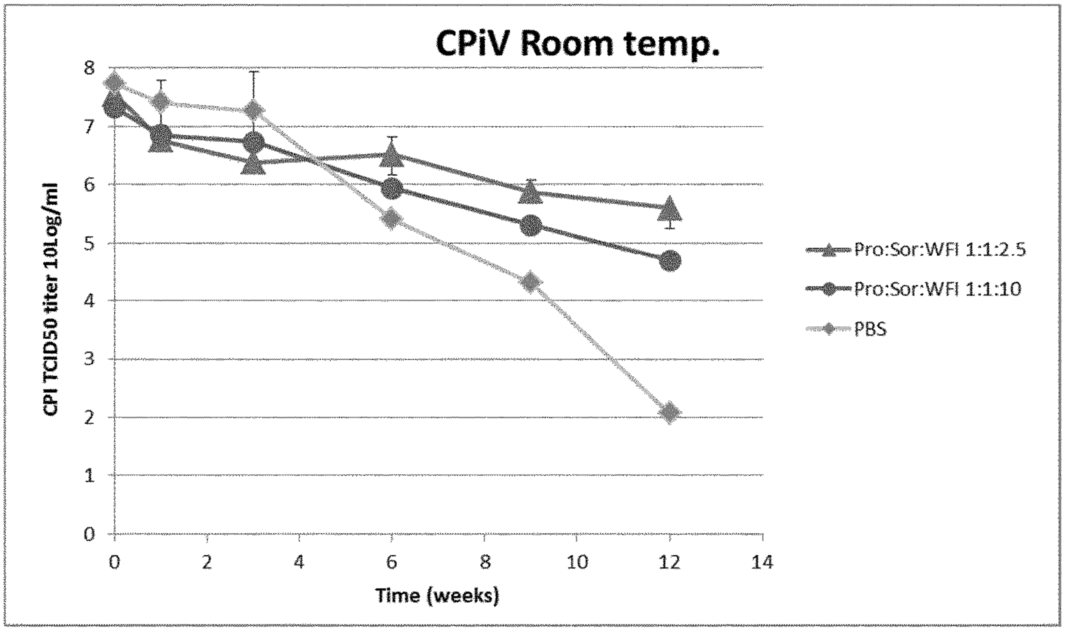

Amounts of live CPiV virus titres remaining after incubation at room temperature (about 20° C.) up to 12 weeks, are presented in FIG. 6. Both compositions were able to significantly reduce virus degradation at this challenging temperature: in NADES 3A titre loss was less than 2 Log 10, in 3B the loss was about 3 Log 10, while in PBS the loss of live CPiV titre was more than 5 Log 10.

Example 5: Variations on Previous Stability Results in NADES-Based Vaccines

To further expand on the experiments in Examples 1-4 above, a number of variations were tested of NADES formulations for the invention.

TABLE 4

Further variations of NADES formulations tested

| # | Ionic species | Polyol | molar ratio Ion. sp:Pol.:WFI | | | wt % water | water activity | Tg (° C.) |
|---|---|---|---|---|---|---|---|---|
| 1A | Betaine | Sucrose | 2.0 | 1.0 | 4.0 | 11.06 | 0.30 | — |
| 3A | Proline | Sorbitol | 1.0 | 1.0 | 2.5 | 13.14 | 0.39 | −41.9 |
| 3B | Proline | Sorbitol | 1.0 | 1.0 | 10.0 | 37.74 | 0.76 | −32.2 |

TABLE 4-continued

Further variations of NADES formulations tested

| # | Ionic species | Polyol | molar ratio Ion. sp:Pol.:WFI | | | wt % water | water activity | Tg (° C.) |
|---|---|---|---|---|---|---|---|---|
| 4 | Choline | Xylitol | 2.0 | 1.0 | 2.5 | 9.49 | 0.18 | −74.8 |
| 5 | Betaine | Sorbitol | 1.0 | 1.0 | 2.5 | 13.07 | 0.32 | −49.9 |
| 6 | Choline | Sorbitol | 1.0 | 1.0 | 2.5 | 12.27 | 0.3 | −77.9 |

In this table, 'Tg' stands for: glass-transition temperature. This was determined using a standard set-up for differential scanning calorimetry. In these measurements, no crystalline phase-transition could be observed for the NADES samples tested in these experiments, only a glass-transition was observed of very small size. Together with the very low Tg values measured, this indicates that these samples do not contain a detectable amount of free water that could form ice-crystals.

The NADES 3B formulation has a water activity of 0.76, which allows the addition of 1/10 volume part of virus in water, to 9/10 volume parts of this NADES, to obtain a liquid vaccine composition according to the invention with a water activity of 0.80.

Figure 7:
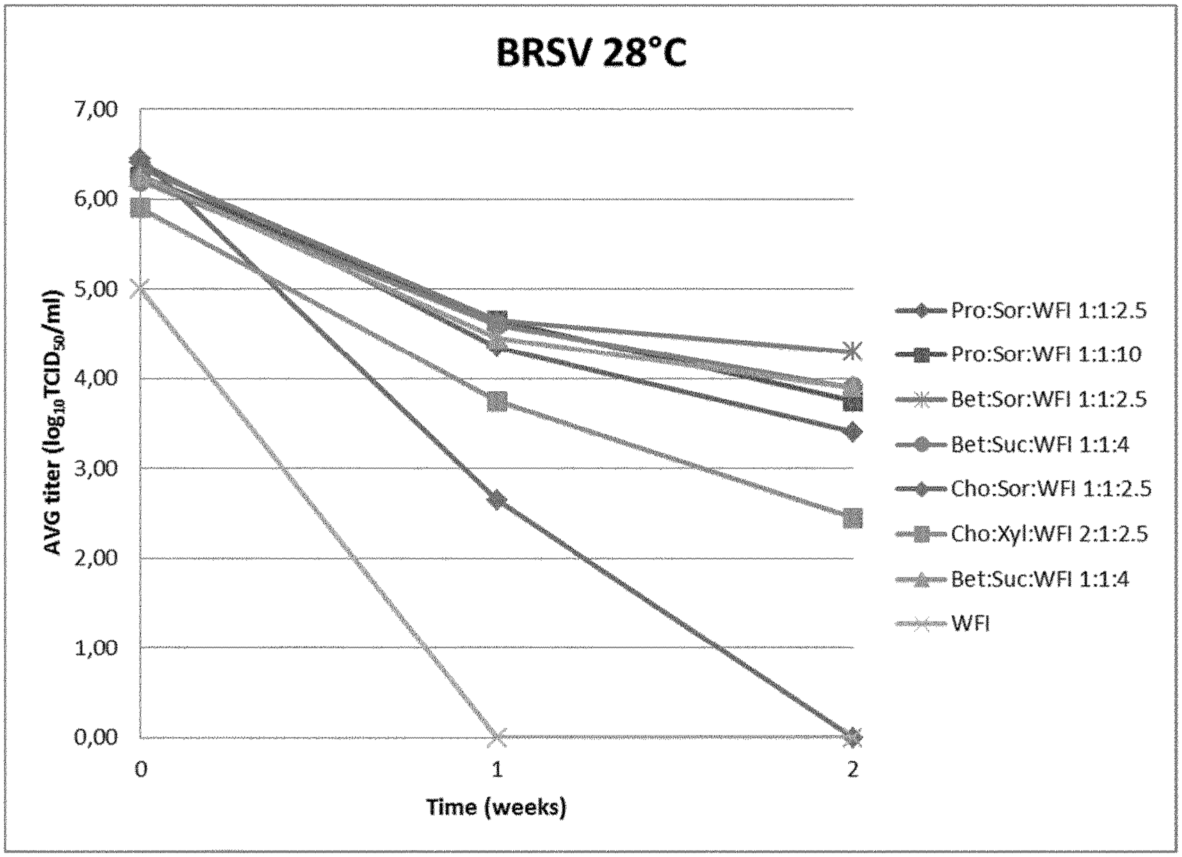

The various NADES formulations were tested in liquid vaccine compositions according to the invention, comprising BRSV. All virus samples were combined with 9 volume parts NADES, mixed, and incubated at 28° C. to perform a forced stability assay. Results are presented in FIG. 7. All NADES formulations listed in Table 4 were able to stabilise BRSV; best results were obtained with NADES using Proline or Betaine as the ionic species.

Example 6: Stability of a Further Paramyxovirus in NADES-Based Vaccines

Canine distemper virus (CVD) is a further Paramyxovirus, like PI3 and CPiV. It is of high veterinary relevance, because of its capability to infect many species of canines and felines. Symptoms include intestinal-, respiratory-, and a variety of systemic signs of disease. Regular vaccinations of cats and dogs against CDV at young age is common. Typically the vaccine is a live attenuated virus, that is produced as a freeze-dried product.

CDV was taken up into a liquid vaccine composition according to the invention, mixed with 9 volume parts NADES 3A (Proline:Sorbitol:WFI at 1:1:2.5 molar ratios). Stability was tested by incubation at 4° C. for up to 16 weeks.

Figure 8:
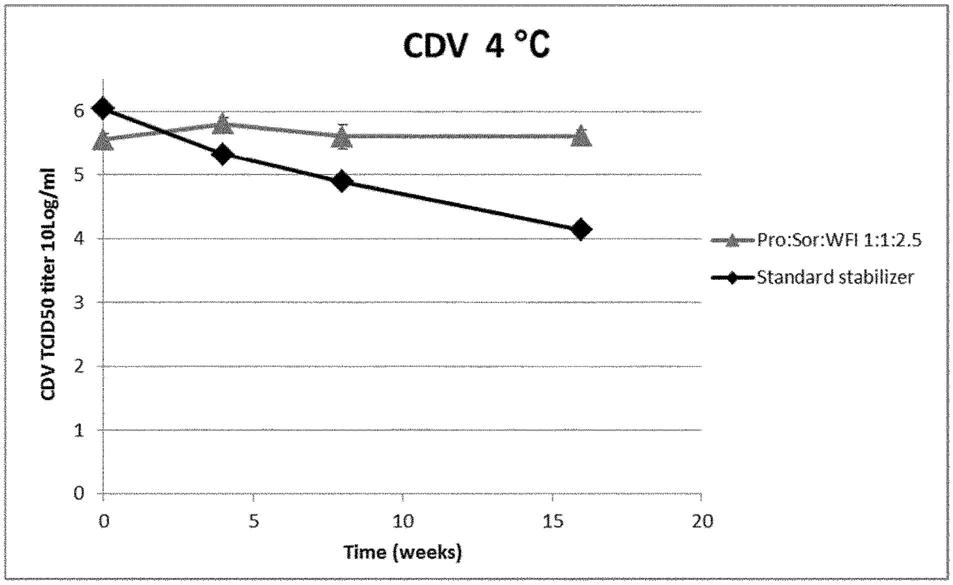

Results are presented in FIG. 8. This shows that a composition based on NADES 3A was able to effectively stabilise CDV at essentially the starting titre, during prolonged storage at refrigerated temperature. The control sample in standard culture medium, showed a persistent drop in titre over time. This difference of stabilisation effect between NADES and control for CDV, is more pronounced than that observed for PI3, see FIG. 2A.

Example 7: Stability of Coronavirus in NADES-Based Vaccines

To assess the stability of a further viral family, a Coronavirus was taken up into liquid vaccine formulations according to the invention. Coronaviruses typically cause (severe) respiratory disease in humans or animals. The virus used was infectious bronchitis virus (IBV), which is an avian Coronavirus.

Like other viruses of its family, IBV is an enveloped virus, and therewith is very sensitive to outside influences. Further, IBV has a positive-sense single-stranded RNA genome, which genome is one of the largest known for RNA viruses. This makes IBV particularly susceptible to degradation upon storage.

IBV has a large impact on the health of poultry such as chickens, and a big negative potential impact on the economy of operation of poultry farming. Most chickens worldwide are vaccinated against IBV infection and disease, and much of those vaccines are live attenuated vaccines, requiring the storage and shipment of live IBV virus up to prolonged periods of time. For a long time, such live attenuated vaccines were therefore produced as freeze-dried product.

To assess the stability of IBV in liquid vaccine formulations based on NADES, the virus was taken up into a variant of NADES 3, namely NADES 3A, composed of: Proline: Sorbitol:Water for injection, in a molar ratio of 1:1:2.5. More characteristics of this formulation are described in Table 4.

The titration of IBV is extremely laborious, as this needs to be done in birds in vivo, or ex vivo on primary cells. A much used, but equally laborious, alternative is titration on embryonated chickens eggs. For this reason only one type of NADES and only one storage temperature was tested in these experiments with IBV.

Materials and Methods:

IBV strain 4/91 was obtained as a standard virus product harvested as the allantoic fluid from inoculated chicken eggs. Virus and NADES were combined 1+9 volume parts, mixed by vortexing, and incubated at 4° C. To be able to titrate all samples on the same batch of eggs, the various timed samples were each prepared fresh, then started incubation, with the longest incubations starting first.

Figure 9:
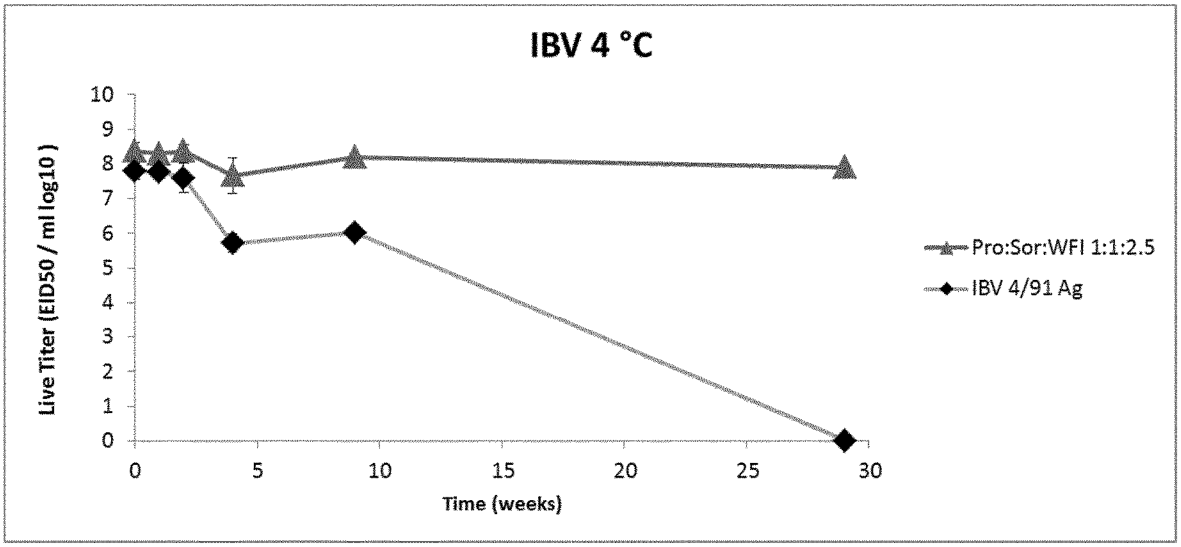

Results and Conclusions:

The results of IBV stability in NADES 3A, up to 30 weeks at 4° C. are depicted in FIG. 9.

From the data in FIG. 9 it is evident that there is a large positive difference in the stabilising effect of the liquid vaccine compositions based on NADES 3A, as compared to the control sample of IBV 4/91 in allantoic fluid: while all virus became degraded in the control samples after 29 weeks at 4° C., the amount of live IBV in NADES 3A remained unaffected, and was not significantly different from the starting titre even after 7 months.

In conclusion, a liquid vaccine composition according to the invention, comprising a Coronavirus, IBV, and a NADES, showed an excellent and unprecedented stabilising effect for the live Coronavirus over a prolonged period of storage.

Example 8: Stability of Herpesvirus in NADES-Based Vaccines

Similar to Example 7, this experiment tested the stabilising effect of a liquid vaccine composition according to the invention on yet a further enveloped virus family: Herpesvirus.

Two representatives were tested: Feline Herpesvirus 1 (FHV1), and Bovine Herpesvirus 1 (BHV1). These viruses are both enveloped viruses with a large double stranded DNA genome. Consequently, from being an enveloped virus, as well as from being a large virus, most Herpesviruses are quite delicate and are known to be prone to rapid degradation under standard storage conditions. Inevitably, live Herpesvirus vaccines are therefore commonly produced as freeze-dried products.

FHV1 causes a contagious and severe respiratory infection in felines, called Feline viral rhinotracheitis. BHV1 is also called Infectious bovine rhinotracheitis virus, and causes similar symptoms in bovines.

Samples of FHV1 and of BHV 1 were obtained from standard cell-cultures.

The FHV1 sample was mixed 1+9 v/v with NADES 3A and with NADES 3B formulations. Next the sample-tubes were mixed for 1 hour on a rotating wheel. Considering the significant in-mixing loss of about 1 Log 10, this method of mixing was probably too violent for this fragile virus.

BHV1 was mixed also with NADES 3A and with NADES 3B, and in addition was also tested in NADES 5 (Betaine: Sorbitol:WFI, at 1:1:2.5 molar ratios). Details are given in Table 4.

Figure 10:
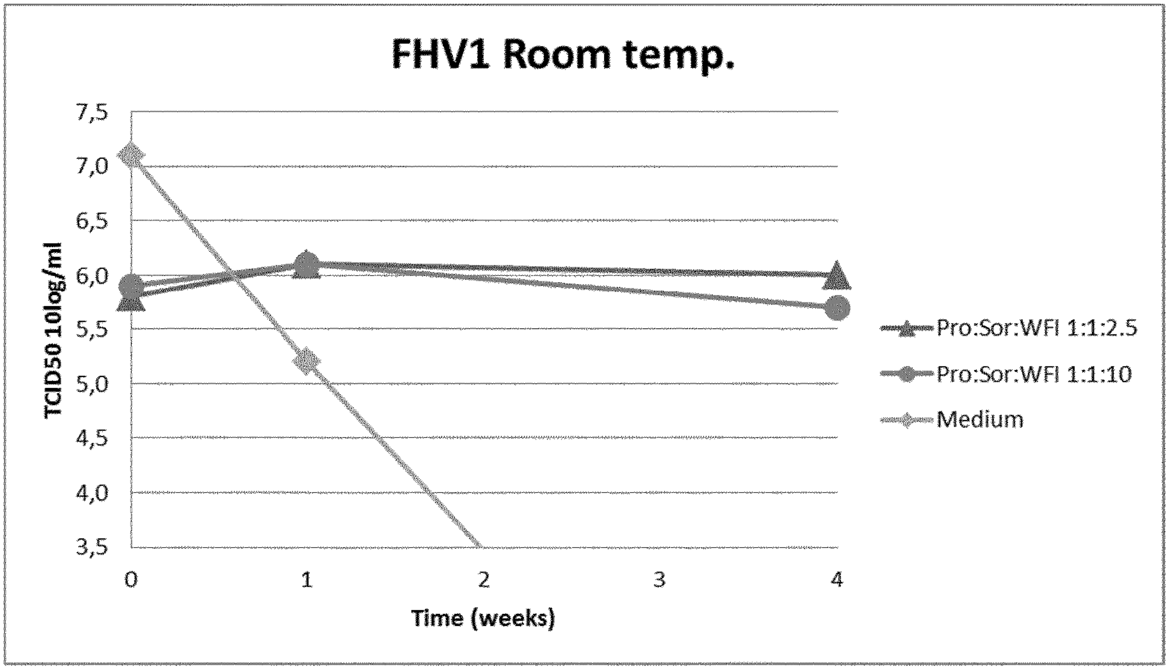
Figure 11:
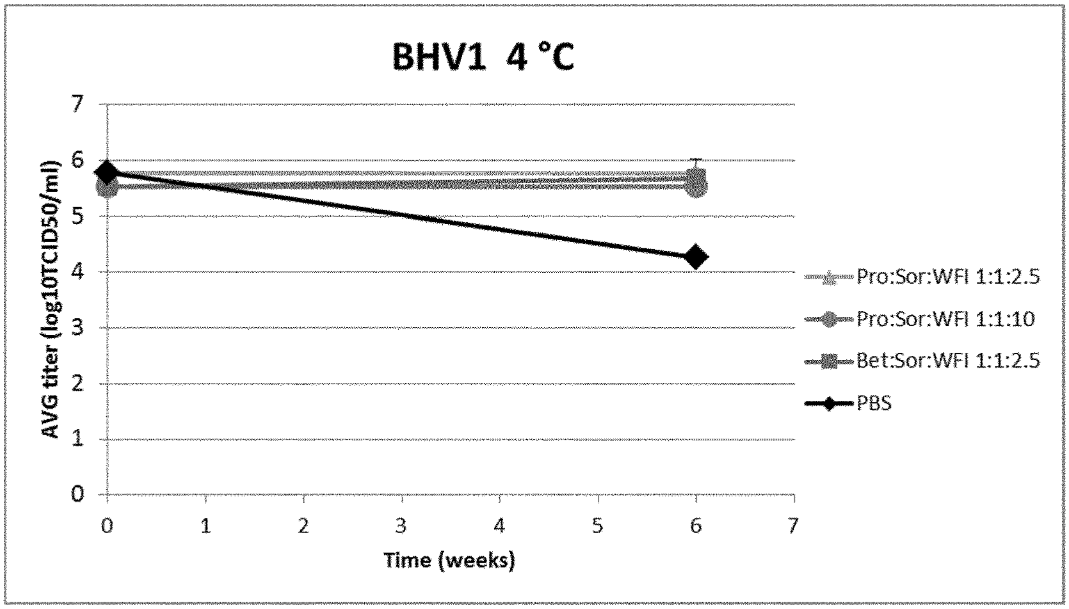

Results and Conclusions:

The results of FHV1 and BHV1 stability in the different liquid vaccine compositions, are presented in FIGS. 10 and 11 respectively.

From the data in FIG. 10 it is clear that FHV1 rapidly degrades in the control composition (standard culture medium). The initial drop in titre at time point zero, is more than compensated later on, as both in NADES 3A and in NADES 3B the live FHV1 was effectively stabilised at essentially the level of the starting titre of the experiment, for up to 4 weeks. Considering that the test temperature in this experiment was room temperature (about 20° C.), which are quite unfavourable conditions for virus stability, this is a remarkably positive result.

Similarly, FIG. 11 indicates that the stability results for BHV1 in the different NADES formulations, at 4° C. are very comparable. All the three NADES tested provided good stabilisation for up to 6 weeks, while the control composition (PBS) showed a clear drop in titre.

In conclusion: a liquid vaccine composition according to the invention, comprising a Herpesvirus, FHV1 or BHV1, and a NADES, showed an excellent stabilising effect for the live Herpesvirus upon storage at a demanding storage temperature, and over a significantly long period.

Example 9: Administration of Vaccine with NADES

To assess the ease of administration, and the safety of a liquid vaccine composition according to the invention in target animals, examples of the vaccine were administered to experimental animals and to post mortem materials.

For this purpose the two variants of the NADES 3 formulation, comprising Proline, Sorbitol, and water for injection, were made and tested: one with high (NADES 3A) and one with low (NADES 3B) viscosity. These served to compare the administration-properties of liquid vaccine compositions according to the invention at two extremes of the viscosity spectrum. The characteristics of these two compositions are described in Table 3. Further, their viscosities were measured using standard conditions: at about 20° C., using a Brookfield™ DV-I+ viscometer, utilising spindle type No. 62, for 30 seconds at 60 r.p.m., in a standard measuring cup of about 80 ml volume.

Handling

The high viscosity NADES, formulation number 3A, could be pushed through a hypodermic needle of size 21 G or less, i.e. a needle with an outer diameter of 0.8 mm or more.

TABLE 5

NADES formulatons tested by administration

| # | Ionic species | Polyol | molar ratio Pro:Sor:WFI | | | Viscosity (mPa · s) |
|---|---|---|---|---|---|---|
| 3A | Proline | Sorbitol | 1.0 | 1.0 | 2.5 | 5197 |
| 3B | Proline | Sorbitol | 1.0 | 1.0 | 10.0 | 33.4 |
| 3C | Proline | Sorbitol | 1.0 | 1.0 | 5.0 | 289 |

Subcutaneous Administration In Vivo

The two NADES formulations tested were compared as placebo's administered by subcutaneous injection, in a safety study in dogs. Special attention was given to any adverse reactions that could occur after the administration of the stabilizer formulations, either locally or systemically.

Both formulations were prepared as described before, by heating and sonification of proline, sorbitol and water for injection, in a closed vial, resulting in a clear and homogeneous liquid. Additionally they were filter-sterilised, and bioburden and endotoxins were determined. Both formulations were found to score below the lowest dilution standard of 1 unit/ml, meeting the general acceptance criteria for sterile formulations. The NADES 3C formulation was prepared by diluting 1 volume part NADES 3A with 9 volume parts WFI, resulting in a formulation with Proline:Sorbitol: WFI in 1:1:5 ratio, and a viscosity of 289 mPa·s. NADES 3B has a viscosity of 33.4 mPa·s.

Six healthy beagle dogs of 7 months old, were divided into two groups of 3 dogs. Each group was assigned to a NADES formulation, and received two doses of 1 ml of the assigned formulation, using a 1 ml syringe and a 21 G 5/8 needle by subcutaneous inoculation, with a two week interval. Group 1 dogs were given the low viscosity NADES 3B, and the Group 2 dogs received the high viscosity NADES 3C. All dogs were clinically monitored daily throughout the study, including for local reactions at the site of the inoculations.

The vaccinations were performed in the scruff of the neck; the first vaccination was done on the left side, and the second vaccination was done on the right side of the neck. The vaccination sites were shaved prior to each administration, and the injection site was circled with a marker pen. No discomfort was observed during any of the injections. At 4 hours post-injection, injection sites were palpated, and little or no material was palpable at the injection sites, and no swelling or redness was observed.

Rectal temperatures were taken on days −3, −2, −1 before each of the vaccinations; at the day of vaccination: just before vaccination and 4 hours after vaccination; and next daily for seven days post vaccination.

Throughout the whole study no significant increase in body temperature was observed in any of the dogs and no clinical adverse effects were observed.

In conclusion: the inoculation of NADES formulations 3C or 3B by subcutaneous route did not induce any adverse inoculation reaction, neither locally, nor systemically.

Intra-Nasal Administration

Two NADES formulations: 3A and 3B were tested for their pattern of spread on the mucosal surface of the nose, when administered intranasally. Both NADES formulations were tested as such, without adding water, consequently, NADES 3A has a viscosity of 5197 mPa·s, and NADES 3B of 33.4 mPa·s. A spatula tip of 'patent blue' colourant was added to 30 ml of each of the NADES formulations, to obtain a deep blue colour. As a control PBS with colourant was used.

Calf heads were obtained post-mortem from calves of about 2-4 weeks old. The administration was done holding the head in an upright position mimicking the position of a calf during i.n. vaccination in the field, with the nostrils tilted slightly upwards.

The liquids were then administered according to a standard procedure for intranasal vaccination, whereby a 2.5 ml syringe without needle, containing 1.5 ml liquid, was placed into a nostril, and then the liquid was squirted out in one steady flow. Next the head was dissected into two halves and the septum was removed and inspected for presence of blue colour in the intranasal tract.

For all samples it was observed that the blue liquids had moved easily through the nasal tract. The low viscosity of the PBS sample allowed for easy injection, but all liquid rushed through quickly. A blue colour was observed all through the whole of the nasal cavity including the beginning of the trachea.

The injection of NADES 3A with the very high viscosity took a little force to inject out of the syringe. Also, as expected, it took longer for the blue liquid to emerge below the head. After dissection of the head, it was observed that also this viscous liquid had spread evenly through the intranasal tract, where it appeared to have formed a thick layer, leaving more material in the nasal tract. This indicates an improved retention and less progression to the upper respiratory tract would occur, when administered to a life calf during i.n. vaccination.

The effect of the administration of the NADES 3B formulation, with the low viscosity, closely resembled that of the PBS sample, where the liquid rushed through the nasal cavity.

In conclusion: it was possible to monitor the distribution of coloured preparations with different viscosity after intranasal injection into calve-heads. Distribution of the liquid as judged by the blue colour was comparable for the two NADES preparations and PBS, with some difference with regard to ease of administration and amount of residual material, whereby the NADES 3A formulation was a little more difficult to eject, but resulted in a thicker layer of residue within the nasal tract. This suggests a delayed release of antigen from such viscous NADES formulations may be obtained.

Example 10: Detailed Analysis of the Proline:Sorbitol:WFI NADES

Figure 12:
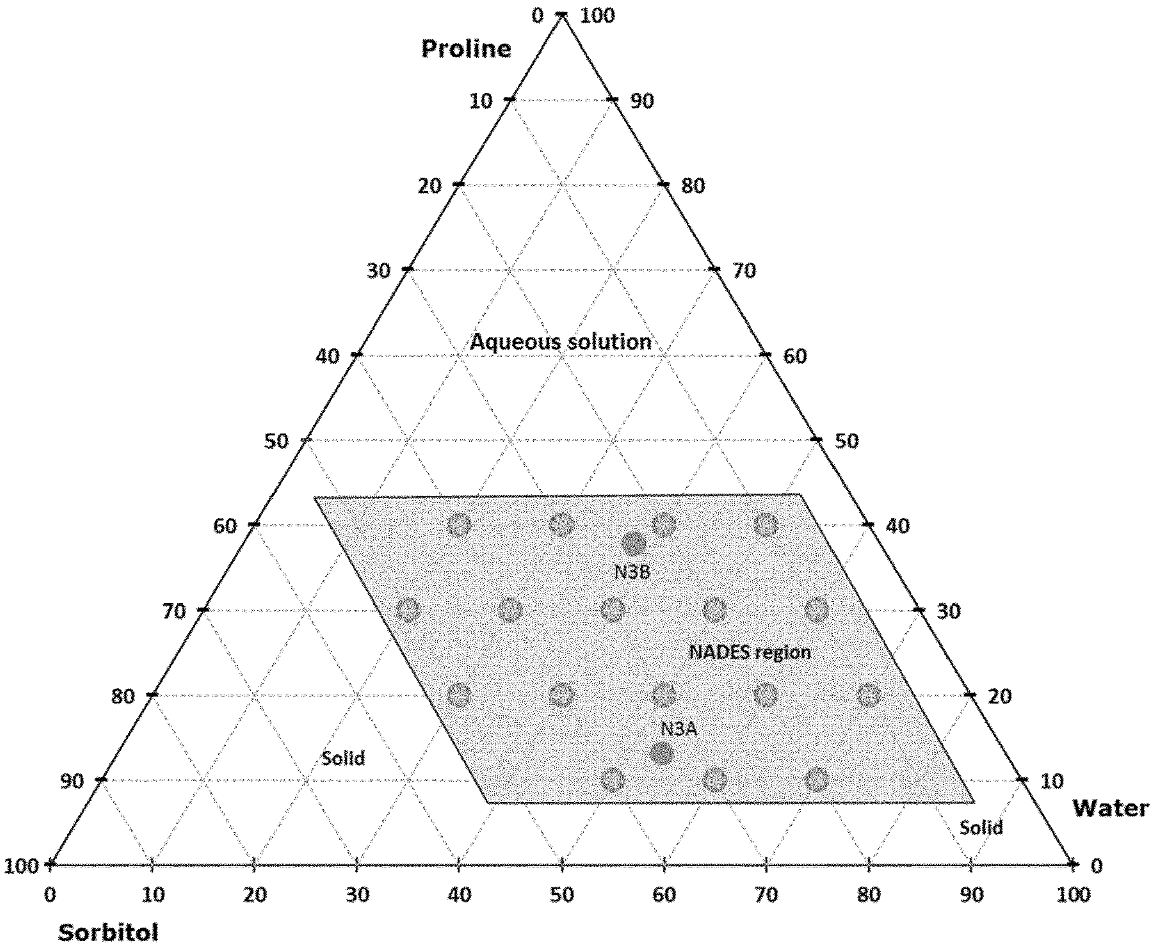

The NADES 3 type formulation, comprising proline, sorbitol, and water for injection, was subjected to detailed analysis. Many variations of ratio's of the three components were made and tested. This is depicted in FIG. 12, which represents a triangle plot of the compositions in weight ratios of the three components. The ratios that were able to generate NADES formulations are presented by the parallelogram inside the triangle. Ratios outside the parallelogram resulted in mixtures that were either solid, or aqueous, as is indicated in the triangle. The various NADES compositions that were tested and found to produce effective and stable variants of NADES 3 are indicated by balls. The specific formulations of NADES 3A and 3B as tested in more detail in the above Examples are also indicated.

LEGEND TO THE FIGURES

FIG. 1:

Stability results of BRSV in different NADES formulations

FIG. 2:

Stability results of bovine PI3 virus in different NADES formulations

FIG. 3:

Stability results of CPiV in different NADES formulations (NADES 1-3 are called stab. 1-3 in the legend; x-axis: time in weeks; y-axis: titre).

FIGS. 4, 5, and 6:

Long term stability results of BRSV, PI3 and CPiV in different NADES formulations, and at different storage temperatures.

FIG. 7:

Stability results for BRSV in variants of NADES formulations

FIGS. 8, 9, 10 and 11:

Stability results of further viruses and virus families: CDV, IBV, FHV1 and BHV1, respectively.

FIG. 12:

Triangle plot of the weight ratios of Proline, Sorbitol, and WFI, made and tested in a detailed analysis of variants of NADES 3. The grey parallelogram indicates effective NADES compositions, the balls indicate individual formulations made and tested.

The invention claimed is:

1. A liquid vaccine composition comprising a live enveloped virus and a pharmaceutically acceptable carrier; wherein the carrier is a natural deep-eutectic solvent (NADES), the vaccine has a water activity between about 0.8 and about 0.1, and wherein the water content in said composition is less than about 50% w/v.

2. The liquid vaccine composition of claim 1, wherein the NADES comprises an organic salt and a polyol.

3. The liquid vaccine composition of claim 2, wherein the organic salt is selected from the group consisting of betaine, proline, carnitine, and choline.

4. The liquid vaccine composition of claim 2, wherein the polyol is a sugar or a sugar-alcohol.

5. The liquid vaccine composition of claim 2, wherein the polyol is selected from the group consisting of sucrose, glycerol, xylitol, and sorbitol.

6. The liquid vaccine composition of claim 1, wherein the enveloped virus has an RNA genome.

7. A method of preparing the liquid vaccine composition of claim 1, comprising the steps of:

a. preparing the NADES, and b. admixing the NADES and a composition comprising the live enveloped viruses.

8. A method of vaccinating a human or animal target, comprising administering the liquid vaccine composition made by the method of claim 7.

9. A kit comprising at least two containers, wherein one container comprises the liquid vaccine composition of claim 1 and one container comprises a liquid diluent.

10. A method of vaccinating a human or animal target, comprising administering the liquid vaccine composition mixed with the diluent that both came in the kit of claim 9.

11. A method of vaccinating a human or animal target caused by a pathogenic form of the live enveloped virus, comprising administering the liquid vaccine composition of claim 1.

* * * * *